United States Patent
Mowry et al.

(10) Patent No.: US 7,326,219 B2
(45) Date of Patent: Feb. 5, 2008

(54) DEVICE FOR PLACING TRANSMYOCARDIAL IMPLANT

(75) Inventors: David H. Mowry, Waconia, MN (US); Robert Edward Kohler, Lake Elmo, MN (US)

(73) Assignee: Wilk Patent Development, New York, NY (US)

( * ) Notice: Subject to any disclaimer, the term of this patent is extended or adjusted under 35 U.S.C. 154(b) by 786 days.

(21) Appl. No.: 10/238,574

(22) Filed: Sep. 9, 2002

(65) Prior Publication Data

US 2004/0049171 A1    Mar. 11, 2004

(51) Int. Cl.
*A61F 11/00* (2006.01)
*A61B 17/10* (2006.01)
*A61B 17/08* (2006.01)

(52) U.S. Cl. .................. 606/108; 606/142; 606/153

(58) Field of Classification Search ............ 606/108, 606/191, 153, 185; 604/164.04, 174, 175, 604/177, 178, 288.01, 890.1; 607/122, 123, 607/129; 623/1.11, 1.36, 1.15, 1.1, 23.7, 623/1.35; 128/898; D24/155
See application file for complete search history.

(56) References Cited

U.S. PATENT DOCUMENTS

| | | | |
|---|---|---|---|
| 4,953,553 A | 9/1990 | Tremulis | |
| 5,193,546 A | 3/1993 | Shaknovich | |
| 5,258,008 A | 11/1993 | Wilk | |
| 5,287,861 A | 2/1994 | Wilk | |
| 5,330,486 A | 7/1994 | Wilk | |
| 5,344,426 A | 9/1994 | Lau et al. | |

(Continued)

FOREIGN PATENT DOCUMENTS

AU    2001281277 B2    11/2001

(Continued)

OTHER PUBLICATIONS

Anne Bohning, Kenneth Jochim & Louis N. Katz; "The Tebesian Vessels as a Source of Nourishment for the Myocardium"; American Journal of Physiology; 1993; pp. 183-200; vol. 106; American Physiological Society; U.S.A.

(Continued)

*Primary Examiner*—Julian W. Woo
(74) *Attorney, Agent, or Firm*—R. Neil Sudol; Henry D. Coleman; William J. Sapone

(57) ABSTRACT

The present invention relates to a transmyocardial implant placement device with an introducer, a transmyocardial implant mounted about the introducer, a wound closure clip engaged to the introducer adjacent the transmyocardial implant. The introducer is adapted to be inserted through a lumen of a coronary vessel and a myocardium of a patient into a chamber of the patient's heart and form a blood flow pathway through the myocardium between the heart chamber and the coronary vessel. When the introducer is inserted, the wound closure clip engages an outer wall of the coronary vessel and the transmyocardial implant extends from the heart chamber to the lumen of the coronary vessel. The transmyocardial implant is expanded in the blood flow pathway and the introducer retracted, leaving the transmyocardial implant in the within the blood flow pathway. As the introducer is retracted, the wound closure clip disengages from the introducer and closes an opening created by the introducer in the outer wall of the coronary vessel.

16 Claims, 10 Drawing Sheets

U.S. PATENT DOCUMENTS

| | | | |
|---|---|---|---|
| 5,389,096 A | 2/1995 | Aita et al. | |
| 5,409,019 A * | 4/1995 | Wilk | 128/898 |
| 5,411,552 A | 5/1995 | Andersen et al. | |
| 5,429,144 A | 7/1995 | Wilk | |
| 5,470,320 A | 11/1995 | Tiefenbrun et al. | |
| 5,554,119 A | 9/1996 | Harrison et al. | |
| 5,593,434 A | 1/1997 | Williams | |
| 5,618,299 A | 4/1997 | Khosravi et al. | |
| 5,662,124 A | 9/1997 | Wilk | |
| 5,733,267 A | 3/1998 | Del Toro | |
| 5,755,682 A | 5/1998 | Knudson et al. | |
| 5,758,663 A | 6/1998 | Wilk et al. | |
| 5,807,384 A | 9/1998 | Mueller | |
| 5,810,836 A * | 9/1998 | Hussein et al. | 606/108 |
| 5,824,071 A | 10/1998 | Nelson et al. | |
| 5,830,222 A | 11/1998 | Makower | |
| 5,840,081 A | 11/1998 | Andersen et al. | |
| 5,876,373 A | 3/1999 | Giba et al. | |
| 5,878,751 A | 3/1999 | Hussein et al. | |
| 5,885,259 A | 3/1999 | Berg | |
| 5,908,028 A | 6/1999 | Wilk | |
| 5,908,029 A | 6/1999 | Knudson et al. | |
| 5,922,022 A | 7/1999 | Nash et al. | |
| 5,925,012 A | 7/1999 | Murphy-Chutorian et al. | |
| 5,931,848 A | 8/1999 | Saadat | |
| 5,935,119 A * | 8/1999 | Guy et al. | 606/185 |
| 5,935,161 A | 8/1999 | Robinson et al. | |
| 5,938,632 A | 8/1999 | Ellis | |
| 5,944,019 A | 8/1999 | Knudson et al. | |
| 5,968,064 A | 10/1999 | Selmon et al. | |
| 5,971,993 A | 10/1999 | Hussein et al. | |
| 5,976,155 A | 11/1999 | Foreman et al. | |
| 5,980,533 A | 11/1999 | Holman | |
| 5,980,548 A | 11/1999 | Evans et al. | |
| 5,984,956 A | 11/1999 | Tweden et al. | |
| 5,997,525 A | 12/1999 | March et al. | |
| 5,999,678 A | 12/1999 | Murphy-Chutorian et al. | |
| 6,004,261 A | 12/1999 | Sinofsky et al. | |
| 6,004,347 A | 12/1999 | McNamara et al. | |
| 6,007,543 A | 12/1999 | Ellis et al. | |
| 6,010,449 A | 1/2000 | Selmon et al. | |
| 6,026,814 A | 2/2000 | LaFontaine et al. | |
| 6,029,672 A | 2/2000 | Vanney et al. | |
| 6,035,856 A | 3/2000 | LaFontaine et al. | |
| 6,036,677 A | 3/2000 | Javier, Jr. et al. | |
| 6,036,697 A | 3/2000 | DiCaprio | |
| 6,045,565 A | 4/2000 | Ellis et al. | |
| 6,053,924 A | 4/2000 | Hussein | |
| 6,053,942 A | 4/2000 | Eno et al. | |
| 6,056,743 A | 5/2000 | Ellis et al. | |
| 6,063,114 A * | 5/2000 | Nash et al. | 623/1.36 |
| 6,067,988 A | 5/2000 | Mueller | |
| 6,068,638 A | 5/2000 | Makower | |
| 6,071,292 A | 6/2000 | Makower et al. | |
| 6,076,529 A | 6/2000 | Vanney et al. | |
| 6,080,163 A | 6/2000 | Hussein et al. | |
| 6,080,170 A | 6/2000 | Nash et al. | |
| 6,092,526 A | 7/2000 | LaFontaine et al. | |
| 6,093,166 A | 7/2000 | Knudson et al. | |
| 6,093,177 A | 7/2000 | Javier, Jr. et al. | |
| 6,093,185 A | 7/2000 | Ellis et al. | |
| D429,334 S * | 8/2000 | Solem | D24/155 |
| 6,102,941 A | 8/2000 | Tweden et al. | |
| 6,113,630 A | 9/2000 | Vanney et al. | |
| 6,113,823 A | 9/2000 | Eno | |
| 6,120,520 A | 9/2000 | Saadat et al. | |
| 6,123,682 A | 9/2000 | Knudson et al. | |
| 6,126,649 A | 10/2000 | VanTassel et al. | |
| 6,126,654 A | 10/2000 | Giba et al. | |
| 6,132,451 A | 10/2000 | Payne et al. | |
| 6,139,541 A | 10/2000 | Vanney et al. | |
| 6,155,264 A | 12/2000 | Ressemann et al. | |
| 6,156,031 A | 12/2000 | Aita et al. | |
| 6,157,852 A | 12/2000 | Selmon et al. | |
| 6,159,225 A | 12/2000 | Makower | |
| 6,165,185 A | 12/2000 | Shennib et al. | |
| 6,165,188 A | 12/2000 | Saadat et al. | |
| 6,168,614 B1 | 1/2001 | Andersen et al. | |
| 6,171,251 B1 | 1/2001 | Mueller et al. | |
| 6,182,668 B1 | 2/2001 | Tweden et al. | |
| 6,186,972 B1 | 2/2001 | Nelson et al. | |
| 6,190,353 B1 | 2/2001 | Makower et al. | |
| 6,193,726 B1 | 2/2001 | Vanney | |
| 6,193,734 B1 | 2/2001 | Bolduc et al. | |
| 6,196,230 B1 * | 3/2001 | Hall et al. | 606/108 |
| 6,197,050 B1 | 3/2001 | Eno et al. | |
| 6,197,324 B1 | 3/2001 | Crittenden | |
| 6,200,311 B1 | 3/2001 | Danek et al. | |
| 6,203,556 B1 | 3/2001 | Evans et al. | |
| 6,213,126 B1 | 4/2001 | LaFontaine et al. | |
| 6,214,041 B1 | 4/2001 | Tweden et al. | |
| 6,217,527 B1 | 4/2001 | Selmon et al. | |
| 6,217,549 B1 | 4/2001 | Selmon et al. | |
| 6,217,575 B1 | 4/2001 | DeVore et al. | |
| 6,221,049 B1 | 4/2001 | Selmon et al. | |
| 6,223,752 B1 | 5/2001 | Vanney et al. | |
| 6,224,584 B1 | 5/2001 | March et al. | |
| 6,231,546 B1 | 5/2001 | Milo et al. | |
| 6,231,551 B1 | 5/2001 | Barbut | |
| 6,231,587 B1 * | 5/2001 | Makower | 606/108 |
| 6,235,000 B1 | 5/2001 | Milo et al. | |
| 6,237,607 B1 | 5/2001 | Vanney et al. | |
| 6,238,406 B1 | 5/2001 | Ellis et al. | |
| 6,241,667 B1 | 6/2001 | Vetter et al. | |
| 6,248,112 B1 | 6/2001 | Gambale et al. | |
| 6,250,305 B1 | 6/2001 | Tweden | |
| 6,251,079 B1 | 6/2001 | Gambale et al. | |
| 6,251,104 B1 | 6/2001 | Kesten et al. | |
| 6,251,116 B1 | 6/2001 | Shennib et al. | |
| 6,251,418 B1 | 6/2001 | Ahern et al. | |
| 6,253,768 B1 | 7/2001 | Wilk | |
| 6,253,769 B1 | 7/2001 | LaFontaine et al. | |
| 6,254,564 B1 | 7/2001 | Wilk et al. | |
| 6,258,052 B1 | 7/2001 | Milo | |
| 6,258,119 B1 | 7/2001 | Hussein et al. | |
| 6,261,304 B1 | 7/2001 | Hall et al. | |
| 6,283,951 B1 | 9/2001 | Flaherty et al. | |
| 6,283,983 B1 | 9/2001 | Makower et al. | |
| 6,285,903 B1 | 9/2001 | Rosenthal et al. | |
| 6,287,317 B1 | 9/2001 | Makower et al. | |
| 6,290,709 B1 | 9/2001 | Ellis et al. | |
| 6,290,728 B1 * | 9/2001 | Phelps et al. | 623/1.15 |
| 6,302,875 B1 | 10/2001 | Makower et al. | |
| 6,302,892 B1 | 10/2001 | Wilk | |
| 6,322,548 B1 | 11/2001 | Payne et al. | |
| 6,330,884 B1 | 12/2001 | Kim | |
| 6,344,027 B1 | 2/2002 | Goll | |
| 6,350,248 B1 | 2/2002 | Knudson et al. | |
| 6,352,543 B1 | 3/2002 | Cole | |
| 6,361,519 B1 | 3/2002 | Knudson et al. | |
| 6,363,938 B2 | 4/2002 | Saadat et al. | |
| 6,363,939 B1 | 4/2002 | Wilk | |
| 6,375,615 B1 | 4/2002 | Flaherty et al. | |
| 6,379,319 B1 | 4/2002 | Garibotto et al. | |
| 6,387,119 B2 | 5/2002 | Wolf et al. | |
| 6,390,098 B1 | 5/2002 | LaFontaine et al. | |
| 6,395,208 B1 | 5/2002 | Herweck et al. | |
| 6,402,740 B1 | 6/2002 | Ellis et al. | |
| 6,406,488 B1 | 6/2002 | Tweden et al. | |
| 6,406,491 B1 | 6/2002 | Vanney | |
| 6,409,697 B2 | 6/2002 | Eno et al. | |
| 6,409,751 B1 | 6/2002 | Hall et al. | |
| 6,416,490 B1 | 7/2002 | Ellis et al. | |
| 6,423,089 B1 | 7/2002 | Gingras et al. | |

| | | |
|---|---|---|
| 6,432,119 B1 | 8/2002 | Saadat |
| 6,432,126 B1 | 8/2002 | Gambale et al. |
| 6,432,127 B1 | 8/2002 | Kim et al. |
| 6,432,132 B1 | 8/2002 | Cottone et al. |
| 6,443,158 B1 | 9/2002 | LaFontaine et al. |
| 6,447,522 B2 | 9/2002 | Gambale et al. |
| 6,447,539 B1 | 9/2002 | Nelson et al. |
| 6,454,760 B2 | 9/2002 | Vanney |
| 6,454,794 B1 | 9/2002 | Knudson et al. |
| 6,458,092 B1 | 10/2002 | Gambale et al. |
| 6,458,140 B2 | 10/2002 | Akin et al. |
| 6,458,323 B1 | 10/2002 | Boekstegers |
| 6,464,709 B1 | 10/2002 | Shennib et al. |
| 6,464,999 B1 * | 10/2002 | Huo et al. ............... 604/890.1 |
| 6,475,226 B1 | 11/2002 | Belef et al. |
| 6,475,244 B2 | 11/2002 | Herweck et al. |
| 6,482,220 B1 | 11/2002 | Mueller |
| 6,491,689 B1 | 12/2002 | Ellis et al. |
| 6,491,707 B2 | 12/2002 | Makower et al. |
| 6,506,408 B1 | 1/2003 | Palasis |
| 6,508,783 B2 | 1/2003 | DeVore |
| 6,508,824 B1 | 1/2003 | Flaherty et al. |
| 6,508,825 B1 | 1/2003 | Selmon et al. |
| 6,511,458 B2 | 1/2003 | Milo et al. |
| 6,514,217 B1 | 2/2003 | Selmon et al. |
| 6,514,271 B2 | 2/2003 | Evans et al. |
| 6,517,527 B2 | 2/2003 | Gambale et al. |
| 6,517,558 B2 | 2/2003 | Gittings et al. |
| 6,524,323 B1 | 2/2003 | Nash et al. |
| 6,524,324 B1 | 2/2003 | Mueller et al. |
| 6,530,914 B1 | 3/2003 | Mickley |
| 6,533,779 B2 | 3/2003 | Kinsella et al. |
| 6,544,220 B2 | 4/2003 | Shuman et al. |
| 6,544,230 B1 | 4/2003 | Flaherty |
| 6,559,132 B1 | 5/2003 | Holmer |
| 6,561,998 B1 | 5/2003 | Roth et al. |
| 6,562,066 B1 | 5/2003 | Martin |
| 6,565,528 B1 | 5/2003 | Mueller |
| 6,565,594 B1 | 5/2003 | Herweck et al. |
| 6,569,145 B1 | 5/2003 | Shmulewitz et al. |
| 6,569,147 B1 | 5/2003 | Evans et al. |
| 6,573,311 B1 | 6/2003 | Martakos et al. |
| 6,575,168 B2 | 6/2003 | LaFontaine et al. |
| 6,579,311 B1 | 6/2003 | Makower |
| 6,582,444 B2 | 6/2003 | Wilk |
| 6,582,463 B1 | 6/2003 | Mowry et al. |
| 6,585,650 B1 | 7/2003 | Solem |
| 6,587,718 B2 | 7/2003 | Talpade |
| 6,589,164 B1 | 7/2003 | Flaherty |
| 6,599,304 B1 | 7/2003 | Selmon et al. |
| 6,602,241 B2 | 8/2003 | Makower et al. |
| 6,605,053 B1 | 8/2003 | Kamm et al. |
| 6,605,113 B2 | 8/2003 | Wilk |
| 6,610,100 B2 | 8/2003 | Phelps et al. |
| 6,613,026 B1 | 9/2003 | Palasis et al. |
| 6,613,081 B2 | 9/2003 | Kim et al. |
| 6,616,626 B2 | 9/2003 | Crank et al. |
| 6,616,675 B1 | 9/2003 | Evard et al. |
| 6,632,470 B2 | 10/2003 | Morra et al. |
| 6,635,214 B2 | 10/2003 | Rapacki et al. |
| 6,638,237 B1 | 10/2003 | Guiles et al. |
| 6,638,247 B1 | 10/2003 | Selmon et al. |
| 6,638,293 B1 | 10/2003 | Makower et al. |
| 6,641,610 B2 | 11/2003 | Wolf et al. |
| 6,651,670 B2 | 11/2003 | Rapacki et al. |
| 6,652,540 B1 | 11/2003 | Cole et al. |
| 6,652,546 B1 | 11/2003 | Nash et al. |
| 6,655,386 B1 | 12/2003 | Makower et al. |
| 6,660,003 B1 | 12/2003 | DeVore et al. |
| 6,660,024 B1 | 12/2003 | Flaherty et al. |
| 6,666,863 B2 | 12/2003 | Wentzel et al. |
| 6,669,691 B1 | 12/2003 | Taimisto |
| 6,669,709 B1 | 12/2003 | Cohn et al. |
| 6,676,695 B2 | 1/2004 | Solem |
| 6,685,648 B2 | 2/2004 | Flaherty et al. |
| 6,685,716 B1 | 2/2004 | Flaherty et al. |
| 6,694,983 B2 | 2/2004 | Wolf et al. |
| 6,701,932 B2 * | 3/2004 | Knudson et al. ............ 128/898 |
| 6,709,425 B2 | 3/2004 | Gambale et al. |
| 6,709,427 B1 | 3/2004 | Nash et al. |
| 6,709,444 B1 | 3/2004 | Makower |
| 6,719,770 B2 | 4/2004 | Laufer et al. |
| 6,726,677 B1 | 4/2004 | Flaherty et al. |
| 6,746,426 B1 | 6/2004 | Flaherty et al. |
| 6,746,464 B1 | 6/2004 | Makower |
| 6,748,258 B1 | 6/2004 | Mueller et al. |
| 6,774,155 B2 | 8/2004 | Martakos et al. |
| 6,774,278 B1 | 8/2004 | Ragheb et al. |
| 6,786,929 B2 | 9/2004 | Gambale et al. |
| 6,802,858 B2 | 10/2004 | Gambale et al. |
| 6,808,498 B2 | 10/2004 | Laroya et al. |
| 6,808,504 B2 | 10/2004 | Schorgl et al. |
| 6,830,568 B1 | 12/2004 | Kesten et al. |
| 6,854,467 B2 | 2/2005 | Boekstegers |
| 6,855,160 B1 | 2/2005 | Gambale et al. |
| 6,863,684 B2 | 3/2005 | Kim et al. |
| 6,878,371 B2 | 4/2005 | Ueno et al. |
| 6,881,199 B2 | 4/2005 | Wilk et al. |
| 6,890,463 B2 | 5/2005 | Martakos et al. |
| 6,893,413 B2 | 5/2005 | Martin |
| 6,913,021 B2 | 7/2005 | Knudson et al. |
| 6,916,304 B2 | 7/2005 | Eno et al. |
| 6,926,690 B2 | 8/2005 | Renati |
| 6,929,009 B2 | 8/2005 | Makower et al. |
| 6,929,011 B2 | 8/2005 | Knudson et al. |
| 6,945,949 B2 | 9/2005 | Wilk |
| 6,949,080 B2 | 9/2005 | Wolf et al. |
| 6,949,118 B2 | 9/2005 | Kohler et al. |
| 6,953,476 B1 | 10/2005 | Shalev |
| 6,953,481 B2 | 10/2005 | Phelps et al. |
| 6,955,681 B2 | 10/2005 | Evans et al. |
| 2001/0000041 A1 | 3/2001 | Selmon et al. |
| 2001/0003985 A1 | 6/2001 | LaFontaine et al. |
| 2001/0004683 A1 | 6/2001 | Gambale et al. |
| 2001/0004690 A1 | 6/2001 | Gambale et al. |
| 2001/0004699 A1 | 6/2001 | Gittings et al. |
| 2001/0008969 A1 | 7/2001 | Evans et al. |
| 2001/0012924 A1 | 8/2001 | Milo et al. |
| 2001/0012948 A1 | 8/2001 | Vanney |
| 2001/0014813 A1 | 8/2001 | Saadat et al. |
| 2001/0016700 A1 | 8/2001 | Eno et al. |
| 2001/0018596 A1 | 8/2001 | Selmon et al. |
| 2001/0020172 A1 | 9/2001 | Selmon et al. |
| 2001/0025643 A1 | 10/2001 | Foley |
| 2001/0027287 A1 | 10/2001 | Shmulewitz et al. |
| 2001/0029385 A1 | 10/2001 | Shennib et al. |
| 2001/0034547 A1 | 10/2001 | Hall et al. |
| 2001/0037117 A1 | 11/2001 | Gambale et al. |
| 2001/0037149 A1 | 11/2001 | Wilk |
| 2001/0039426 A1 | 11/2001 | Makower et al. |
| 2001/0039445 A1 | 11/2001 | Hall et al. |
| 2001/0041902 A1 | 11/2001 | Lepulu et al. |
| 2001/0044631 A1 | 11/2001 | Akin et al. |
| 2001/0047165 A1 | 11/2001 | Makower et al. |
| 2001/0047197 A1 | 11/2001 | Foley |
| 2001/0049523 A1 | 12/2001 | DeVore et al. |
| 2001/0053932 A1 | 12/2001 | Phelps et al. |
| 2002/0002349 A1 | 1/2002 | Flaherty et al. |
| 2002/0004662 A1 | 1/2002 | Wilk |
| 2002/0004663 A1 | 1/2002 | Gittings et al. |
| 2002/0007138 A1 | 1/2002 | Wilk et al. |
| 2002/0029079 A1 | 3/2002 | Kim et al. |
| 2002/0032476 A1 | 3/2002 | Gambale et al. |
| 2002/0032478 A1 | 3/2002 | Boekstegers et al. |
| 2002/0033180 A1 | 3/2002 | Solem |
| 2002/0045928 A1 | 4/2002 | Boekstegers |

| | | |
|---|---|---|
| 2002/0049486 A1 | 4/2002 | Knudson et al. |
| 2002/0049495 A1 | 4/2002 | Kutryk et al. |
| 2002/0058897 A1 | 5/2002 | Renati |
| 2002/0062146 A1 | 5/2002 | Makower et al. |
| 2002/0065478 A1 | 5/2002 | Knudson et al. |
| 2002/0072699 A1 | 6/2002 | Knudson et al. |
| 2002/0072758 A1 | 6/2002 | Reo et al. |
| 2002/0077566 A1 | 6/2002 | Laroya et al. |
| 2002/0077654 A1 | 6/2002 | Javier, Jr. et al. |
| 2002/0082546 A1 | 6/2002 | Crank et al. |
| 2002/0092535 A1 | 7/2002 | Wilk |
| 2002/0092536 A1 | 7/2002 | LaFontaine et al. |
| 2002/0095110 A1 | 7/2002 | Vanney et al. |
| 2002/0095111 A1 | 7/2002 | Tweden et al. |
| 2002/0095206 A1 | 7/2002 | Addonizio et al. |
| 2002/0099392 A1 | 7/2002 | Mowry et al. |
| 2002/0099404 A1 | 7/2002 | Mowry |
| 2002/0100484 A1 | 8/2002 | Hall et al. |
| 2002/0103459 A1 | 8/2002 | Sparks et al. |
| 2002/0103495 A1 | 8/2002 | Cole |
| 2002/0103534 A1 | 8/2002 | Vanney et al. |
| 2002/0111644 A1 | 8/2002 | Shuman et al. |
| 2002/0111672 A1 | 8/2002 | Kim et al. |
| 2002/0123698 A1 | 9/2002 | Garibotto et al. |
| 2002/0123786 A1 | 9/2002 | Gittings et al. |
| 2002/0138087 A1 | 9/2002 | Shennib et al. |
| 2002/0143285 A1 | 10/2002 | Eno et al. |
| 2002/0143289 A1 | 10/2002 | Ellis et al. |
| 2002/0143347 A1 | 10/2002 | Cole et al. |
| 2002/0144696 A1 | 10/2002 | Sharkawy et al. |
| 2002/0161383 A1 | 10/2002 | Akin et al. |
| 2002/0161424 A1 | 10/2002 | Rapacki et al. |
| 2002/0165479 A1 | 11/2002 | Wilk |
| 2002/0165606 A1 | 11/2002 | Wolf et al. |
| 2002/0179098 A1 | 12/2002 | Makower et al. |
| 2002/0183716 A1 | 12/2002 | Herweck et al. |
| 2002/0193782 A1 | 12/2002 | Ellis et al. |
| 2003/0015816 A1 | 1/2003 | Rapacki et al. |
| 2003/0018379 A1 | 1/2003 | Knudson et al. |
| 2003/0044315 A1 | 3/2003 | Boekstegers |
| 2003/0045828 A1 | 3/2003 | Wilk |
| 2003/0055371 A1 | 3/2003 | Wolf et al. |
| 2003/0062650 A1 | 4/2003 | Martakos et al. |
| 2003/0069532 A1 | 4/2003 | Mowry et al. |
| 2003/0069587 A1 | 4/2003 | Schorgl et al. |
| 2003/0073973 A1 | 4/2003 | Evans et al. |
| 2003/0074006 A1 | 4/2003 | Mowry et al. |
| 2003/0078561 A1 | 4/2003 | Gambale et al. |
| 2003/0078562 A1 | 4/2003 | Makower et al. |
| 2003/0083678 A1 | 5/2003 | Herweck et al. |
| 2003/0097172 A1 | 5/2003 | Shalev et al. |
| 2003/0100920 A1 | 5/2003 | Akin et al. |
| 2003/0105514 A1 | 6/2003 | Phelps et al. |
| 2003/0114872 A1 | 6/2003 | Mueller et al. |
| 2003/0120195 A1 | 6/2003 | Milo et al. |
| 2003/0120259 A1 | 6/2003 | Mickley |
| 2003/0125798 A1 | 7/2003 | Martin |
| 2003/0130611 A1 | 7/2003 | Martin |
| 2003/0130719 A1 | 7/2003 | Martin |
| 2003/0135260 A1 | 7/2003 | Kohler et al. |
| 2003/0149126 A1 | 8/2003 | Martakos et al. |
| 2003/0149474 A1 | 8/2003 | Becker |
| 2003/0153901 A1 | 8/2003 | Herweck et al. |
| 2003/0158509 A1 | 8/2003 | Tweden et al. |
| 2003/0158573 A1 | 8/2003 | Gittings et al. |
| 2003/0163198 A1 | 8/2003 | Morra et al. |
| 2003/0171800 A1 | 9/2003 | Bicek et al. |
| 2003/0181938 A1 | 9/2003 | Roth et al. |
| 2003/0191449 A1 | 10/2003 | Nash et al. |
| 2003/0195457 A1 | 10/2003 | LaFontaine et al. |
| 2003/0195458 A1 | 10/2003 | Phelps et al. |
| 2003/0195606 A1 | 10/2003 | Davidson et al. |
| 2003/0204160 A1 | 10/2003 | Kamm et al. |
| 2003/0212413 A1 | 11/2003 | Wilk |
| 2003/0216678 A1 | 11/2003 | March et al. |
| 2003/0216679 A1 | 11/2003 | Wolf et al. |
| 2003/0216801 A1 | 11/2003 | Tweden et al. |
| 2003/0220661 A1 | 11/2003 | Mowry et al. |
| 2003/0225425 A1 | 12/2003 | Kupiecki et al. |
| 2003/0229366 A1 | 12/2003 | Reggie et al. |
| 2003/0236542 A1 | 12/2003 | Makower |
| 2004/0006298 A1 | 1/2004 | Wilk |
| 2004/0006301 A1 | 1/2004 | Sell et al. |
| 2004/0015193 A1 | 1/2004 | Lamson et al. |
| 2004/0015225 A1 | 1/2004 | Kim et al. |
| 2004/0019348 A1 | 1/2004 | Stevens et al. |
| 2004/0037946 A1 | 2/2004 | Morra et al. |
| 2004/0044392 A1 | 3/2004 | Von Oepen |
| 2004/0058097 A1 | 3/2004 | Weder |
| 2004/0059280 A1 | 3/2004 | Makower et al. |
| 2004/0073157 A1 | 4/2004 | Knudson et al. |
| 2004/0073238 A1 | 4/2004 | Makower |
| 2004/0077987 A1 | 4/2004 | Rapacki et al. |
| 2004/0077988 A1 | 4/2004 | Tweden et al. |
| 2004/0077990 A1 | 4/2004 | Knudson et al. |
| 2004/0088042 A1 | 5/2004 | Kim et al. |
| 2004/0106931 A1 | 6/2004 | Guiles et al. |
| 2004/0113306 A1 | 6/2004 | Rapacki et al. |
| 2004/0118415 A1 | 6/2004 | Hall et al. |
| 2004/0122318 A1 | 6/2004 | Flaherty et al. |
| 2004/0122347 A1 | 6/2004 | Knudson et al. |
| 2004/0133154 A1 | 7/2004 | Flaherty et al. |
| 2004/0133225 A1 | 7/2004 | Makower |
| 2004/0138562 A1 | 7/2004 | Makower et al. |
| 2004/0147837 A1 | 7/2004 | Mccauley et al. |
| 2004/0147869 A1 | 7/2004 | Wolf et al. |
| 2004/0158143 A1 | 8/2004 | Flaherty et al. |
| 2004/0158227 A1 | 8/2004 | Nash et al. |
| 2004/0167444 A1 | 8/2004 | Laroya et al. |
| 2004/0168691 A1 | 9/2004 | Sharkawy et al. |
| 2004/0186507 A1 | 9/2004 | Hall et al. |
| 2004/0186557 A1 | 9/2004 | Gambale et al. |
| 2004/0186587 A1 | 9/2004 | Ahern |
| 2004/0210190 A1 | 10/2004 | Kohler et al. |
| 2004/0210304 A1 | 10/2004 | Seguin et al. |
| 2004/0219180 A1 | 11/2004 | Gambale et al. |
| 2004/0220598 A1 | 11/2004 | Bolduc et al. |
| 2004/0225355 A1 | 11/2004 | Stevens |
| 2004/0232587 A1 | 11/2004 | Martakos et al. |
| 2004/0236418 A1 | 11/2004 | Stevens |
| 2004/0243219 A1 | 12/2004 | Fischer et al. |
| 2004/0254451 A1 | 12/2004 | Mueller et al. |
| 2005/0004505 A1 | 1/2005 | Phelps et al. |
| 2005/0004558 A1 | 1/2005 | Gambale et al. |
| 2005/0004648 A1 | 1/2005 | Boekstegers |
| 2005/0033220 A1 | 2/2005 | Wilk et al. |
| 2005/0043781 A1 | 2/2005 | Foley |
| 2005/0055081 A1 | 3/2005 | Goodwin et al. |
| 2005/0055082 A1 | 3/2005 | Ben Muvhar et al. |
| 2005/0060019 A1 | 3/2005 | Gambale et al. |
| 2005/0090748 A1 | 4/2005 | Makower et al. |
| 2005/0101903 A1 | 5/2005 | Kohler et al. |
| 2005/0101904 A1 | 5/2005 | Wilk |
| 2005/0119731 A1 | 6/2005 | Brucker et al. |
| 2005/0159726 A1 | 7/2005 | Evans et al. |

FOREIGN PATENT DOCUMENTS

| | | |
|---|---|---|
| AU | 757647 B2 | 2/2003 |
| AU | 776895 B2 | 9/2004 |
| AU | 777443 B2 | 10/2004 |
| AU | 778831 B2 | 12/2004 |
| AU | 2004231189 A1 | 12/2004 |
| AU | 2004242527 A1 | 1/2005 |
| CA | 2378589 A1 | 2/2001 |
| CA | 2381192 A1 | 2/2001 |

| | | | | | | |
|---|---|---|---|---|---|---|
| CA | 2385662 | A1 | 3/2001 | WO | WO 99/15220 A1 | 4/1999 |
| CA | 2407987 | A1 | 11/2001 | WO | WO 99/17671 A1 | 4/1999 |
| CA | 2418958 | A1 | 2/2002 | WO | WO 99/17683 A1 | 4/1999 |
| CA | 2435962 | A1 | 8/2002 | WO | WO 99/21490 A1 | 5/1999 |
| CA | 2457755 | A1 | 2/2003 | WO | WO 99/21510 A1 | 5/1999 |
| EP | 0 592 410 | B1 | 10/1995 | WO | WO 99/22655 A1 | 5/1999 |
| EP | 0 732 088 | A2 | 9/1996 | WO | WO 99/22658 A1 | 5/1999 |
| EP | 0 792 624 | A1 | 9/1997 | WO | WO 99/25273 A1 | 5/1999 |
| EP | 0 797 957 | A1 | 10/1997 | WO | WO 99/27985 A1 | 6/1999 |
| EP | 0 797 958 | A1 | 10/1997 | WO | WO 99/35977 A1 | 7/1999 |
| EP | 0 799 604 | A1 | 10/1997 | WO | WO 99/35979 A1 | 7/1999 |
| EP | 0 801 928 | A1 | 10/1997 | WO | WO 99/35980 A1 | 7/1999 |
| EP | 0 815 798 | A2 | 1/1998 | WO | WO 99/36000 A1 | 7/1999 |
| EP | 0 829 239 | A1 | 3/1998 | WO | WO 99/36001 A1 | 7/1999 |
| EP | 0 836 834 | A2 | 4/1998 | WO | WO 99/38459 A2 | 8/1999 |
| EP | 0 853 921 | A2 | 7/1998 | WO | WO 99/40853 A1 | 8/1999 |
| EP | 0 858 779 | A1 | 8/1998 | WO | WO 99/40868 A1 | 8/1999 |
| EP | 0 876 796 | A2 | 11/1998 | WO | WO 99/40963 A1 | 8/1999 |
| EP | 0 876 803 | A2 | 11/1998 | WO | WO 99/44524 A2 | 9/1999 |
| EP | 0 888 750 | A1 | 1/1999 | WO | WO 99/48545 A1 | 9/1999 |
| EP | 0 895 752 | A1 | 2/1999 | WO | WO 99/48549 A2 | 9/1999 |
| EP | 0 934 728 | A2 | 8/1999 | WO | WO 99/49793 A1 | 10/1999 |
| EP | 1 020 166 | A1 | 7/2000 | WO | WO 99/49910 A1 | 10/1999 |
| EP | 1 027 870 | A1 | 8/2000 | WO | WO 99/51162 A1 | 10/1999 |
| EP | 1 088 564 | A1 | 4/2001 | WO | WO 99/53863 A1 | 10/1999 |
| EP | 1 097 676 | A1 | 5/2001 | WO | WO 99/55406 A1 | 11/1999 |
| EP | 1 166 721 | A2 | 1/2002 | WO | WO 99/60941 A1 | 12/1999 |
| EP | 0 959 815 | A1 | 12/2002 | WO | WO 99/62430 A1 | 12/1999 |
| EP | 1 112 097 | A1 | 6/2003 | WO | WO 00/09195 A1 | 2/2000 |
| EP | 0 954 248 | B1 | 9/2004 | WO | WO 00/12029 A1 | 3/2000 |
| EP | 1 115 452 | B1 | 11/2004 | WO | WO 00/13722 A1 | 3/2000 |
| EP | 1 477 202 | A2 | 11/2004 | WO | WO 00/15146 A1 | 3/2000 |
| EP | 1 107 710 | B1 | 12/2004 | WO | WO 00/15147 A1 | 3/2000 |
| EP | 1 484 081 | A1 | 12/2004 | WO | WO 00/15148 A1 | 3/2000 |
| EP | 1 143 879 | B1 | 3/2005 | WO | WO 00/15149 A1 | 3/2000 |
| EP | 1 516 599 | A2 | 3/2005 | WO | WO 00/15275 A2 | 3/2000 |
| EP | 1 522 278 | A1 | 4/2005 | WO | WO 00/16848 A1 | 3/2000 |
| EP | 1 547 533 | A2 | 6/2005 | WO | WO 00/18302 A2 | 4/2000 |
| EP | 1 027 013 | B1 | 8/2005 | WO | WO 00/18323 A2 | 4/2000 |
| EP | 1 067 869 | B1 | 11/2005 | WO | WO 00/18325 A1 | 4/2000 |
| EP | 1 021 141 | B1 | 1/2006 | WO | WO 00/18326 A1 | 4/2000 |
| GB | 2 316 322 | B | 10/1998 | WO | WO 00/18331 A2 | 4/2000 |
| WO | WO 96/32972 | A1 | 10/1996 | WO | WO 00/18462 A2 | 4/2000 |
| WO | WO 96/35469 | A1 | 11/1996 | WO | WO 00/21436 A1 | 4/2000 |
| WO | WO 96/39962 | A1 | 12/1996 | WO | WO 00/21461 A2 | 4/2000 |
| WO | WO 96/39964 | A1 | 12/1996 | WO | WO 00/21463 A1 | 4/2000 |
| WO | WO 96/39965 | A1 | 12/1996 | WO | WO 00/24449 A1 | 5/2000 |
| WO | WO 97/13463 | A1 | 4/1997 | WO | WO 00/33725 A2 | 6/2000 |
| WO | WO 97/13471 | A1 | 4/1997 | WO | WO 00/35376 A1 | 6/2000 |
| WO | WO 97/27893 | A1 | 8/1997 | WO | WO 00/36997 A1 | 6/2000 |
| WO | WO 97/27897 | A1 | 8/1997 | WO | WO 00/41632 A1 | 7/2000 |
| WO | WO 97/27898 | A1 | 8/1997 | WO | WO 00/41633 A1 | 7/2000 |
| WO | WO 97/32551 | A1 | 9/1997 | WO | WO 00/43051 A1 | 7/2000 |
| WO | WO 97/43961 | A1 | 11/1997 | WO | WO 00/45711 A1 | 8/2000 |
| WO | WO 98/03118 | A1 | 1/1998 | WO | WO 00/45886 A2 | 8/2000 |
| WO | WO 98/06356 | A1 | 2/1998 | WO | WO 00/49952 A1 | 8/2000 |
| WO | WO 98/10714 | A1 | 3/1998 | WO | WO 00/49954 A2 | 8/2000 |
| WO | WO 98/16161 | A1 | 4/1998 | WO | WO 00/49956 A1 | 8/2000 |
| WO | WO 98/24373 | A1 | 6/1998 | WO | WO 00/54660 A1 | 9/2000 |
| WO | WO 98/25533 | A1 | 6/1998 | WO | WO 00/54661 A1 | 9/2000 |
| WO | WO 98/38916 | A1 | 9/1998 | WO | WO 00/56224 A1 | 9/2000 |
| WO | WO 98/38925 | A1 | 9/1998 | WO | WO 00/56225 A1 | 9/2000 |
| WO | WO 98/38939 | A1 | 9/1998 | WO | WO 00/56387 A1 | 9/2000 |
| WO | WO 98/38941 | A1 | 9/1998 | WO | WO 00/66007 A1 | 11/2000 |
| WO | WO 98/39038 | A1 | 9/1998 | WO | WO 00/66009 A1 | 11/2000 |
| WO | WO 98/46115 | A2 | 10/1998 | WO | WO 00/66035 A1 | 11/2000 |
| WO | WO 98/46119 | A1 | 10/1998 | WO | WO 00/69345 A1 | 11/2000 |
| WO | WO 98/49964 | A1 | 11/1998 | WO | WO 00/69504 A1 | 11/2000 |
| WO | WO 98/57590 | A1 | 12/1998 | WO | WO 00/71195 A1 | 11/2000 |
| WO | WO 98/57591 | A1 | 12/1998 | WO | WO 01/08566 A1 | 2/2001 |
| WO | WO 98/57592 | A1 | 12/1998 | WO | WO 01/08602 A1 | 2/2001 |
| WO | WO 99/07296 | A1 | 2/1999 | WO | WO 01/10340 A1 | 2/2001 |
| WO | WO 99/08624 | A1 | 2/1999 | WO | WO 01/10341 A2 | 2/2001 |

| | | |
|---|---|---|
| WO | WO 01/10347 A1 | 2/2001 |
| WO | WO 01/10348 A1 | 2/2001 |
| WO | WO 01/10349 A1 | 2/2001 |
| WO | WO 01/10350 A1 | 2/2001 |
| WO | WO 01/17440 A1 | 3/2001 |
| WO | WO 01/17456 A1 | 3/2001 |
| WO | WO 01/23016 A1 | 4/2001 |
| WO | WO 01/41657 A1 | 6/2001 |
| WO | WO 01/49187 A1 | 7/2001 |
| WO | WO 01/68158 A1 | 9/2001 |
| WO | WO 01/70133 A2 | 9/2001 |
| WO | WO 01/72239 A2 | 10/2001 |
| WO | WO 01/78801 A2 | 10/2001 |
| WO | WO 01/82803 A1 | 11/2001 |
| WO | WO 01/82837 A2 | 11/2001 |
| WO | WO 02/11647 A2 | 2/2002 |
| WO | WO 02/11807 A2 | 2/2002 |
| WO | WO 02/13698 A1 | 2/2002 |
| WO | WO 02/13699 A1 | 2/2002 |
| WO | WO 02/13703 A1 | 2/2002 |
| WO | WO 02/13704 A1 | 2/2002 |
| WO | WO 02/24108 A2 | 3/2002 |
| WO | WO 02/24247 A1 | 3/2002 |
| WO | WO 02/24248 A1 | 3/2002 |
| WO | WO 02/26310 A1 | 4/2002 |
| WO | WO 02/26462 A1 | 4/2002 |
| WO | WO 02/30325 A2 | 4/2002 |
| WO | WO 02/30326 A2 | 4/2002 |
| WO | WO 02/30330 A2 | 4/2002 |
| WO | WO 02/32330 A2 | 4/2002 |
| WO | WO 02/34323 A2 | 5/2002 |
| WO | WO 02/45598 A2 | 6/2002 |
| WO | WO 02/49465 A2 | 6/2002 |
| WO | WO 02/056937 A2 | 7/2002 |
| WO | WO 02/058567 A2 | 8/2002 |
| WO | WO 02/058591 A2 | 8/2002 |
| WO | WO 02/060509 A1 | 8/2002 |
| WO | WO 02/062265 A2 | 8/2002 |
| WO | WO 02/064020 A2 | 8/2002 |
| WO | WO 02/071974 A2 | 9/2002 |
| WO | WO 02/074175 A2 | 9/2002 |
| WO | WO 02/091958 A1 | 11/2002 |
| WO | WO 03/008005 A2 | 1/2003 |
| WO | WO 03/015638 A2 | 2/2003 |
| WO | WO 03/017870 A1 | 3/2003 |
| WO | WO 03/024307 A2 | 3/2003 |
| WO | WO 03/028522 A2 | 4/2003 |
| WO | WO 03/030744 A1 | 4/2003 |
| WO | WO 03/030784 A1 | 4/2003 |
| WO | WO 03/041469 A2 | 5/2003 |
| WO | WO 03/079932 A2 | 10/2003 |
| WO | WO 2004/000170 A1 | 12/2003 |
| WO | WO 2004/014257 A1 | 2/2004 |
| WO | WO 2004/014474 A1 | 2/2004 |

OTHER PUBLICATIONS

Alfred Goldman, Seymour M. Greenstone, Fred S. Preuss, Sherman H. Strauss & En-Shu Chang; "Experimental Methods for Producing a Collateral Circulation to the Heart Directly from the Left Ventricle"; Journal of Thoracic Surgery; Mar. 1956; pp. 364-374; vol. 31, No. 3; U.S.A.

C. Massimo & L. Boffi; "Myocardial, Revascularization by a New Method of Carrying Blood Directly From the Left Ventricular Cavity into the Coronary Circulation"; Journal of Thoracic Surgery; Aug. 1957; pp. 257-264; vol. 34; U.S.A.

Banning G. Lary & Roger W. Sherman; "A method for creating a coronary-myocardial artery"; Surgery; Jun. 1966; pp. 1061-1064; vol. 59, No. 6; The C.V. Mosby Company; St. Louis, MO.

Akio Wakayabashi, Solomon T. Little, Jr. & John E. Connolly; "Myocardial Boring for the Ischemic Heart"; Archives of Surgery; Nov. 1967; pp. 743-752; vol. 95; American Medical Association; U.S.A.

Julio C. Palmaz, Francisco Garcia, Randy R. Sibbitt, Fremin O. Tio, David T. Kopp, Wayne Schwesinger, Jack L. Lancaster & Peter Chang; "Expandable Intrahepatic Portacaval Shunt Stents in Dogs with Chronic Portal Hypertension"; American Journal of Roentgenology; Dec. 1986; pp. 1251-1254; vol. 147; The American Roentgen Ray Society; U.S.A.

Banning G. Lary, Antonio Camelo, Roger W. Sherman & Thomas J. Noto; "Myocardial Revascularization Experiments Using the Epicardium"; Archives of Surgery.; Jan. 1969; pp. 69-72; vol. 98; American Medical Association; U.S.A.

Ladislav Kuzela & George E. Miller, Jr.; "Experimental evaluation of direct transventricular revascularization"; Journal of Thoracic and Cardiovascular Surgery; Jun. 1969; pp. 770-773; vol. 57, No. 6; The C.V. Mosby Company; St. Louis, MO.

Ian Munro & Peter Allen; "The possibility of myocardial revascularization by creation of a left ventriculocoronary artery fistula"; The Journal of Thoracic and Cardiovascular Surgery; Jul. 1969; pp. 25-32; vol. 58, No. 1; The C.V. Mosby Company; St. Louis, MO.

Isam N. Anabtawi, Hubert F. Reigler, & Robert G. Ellison;"Experimental evaluation of myocardial tunnelization as a method of myocardial revascularization"; Journal of Thoracic and Cardiovascular Surgery; Nov. 1969; pp. 638-646; vol. 58, No. 5; The C.V. Mosby Company; St. Louis, MO.

Robert J. Gardner, Benjamin L. Plybon & Herbert E. Warden; "An Experimental Anatomic Study of Indirect Myocardial Revascularization"; Journal of Surgical Research; 1971; pp. 243-247; vol. 11; Academic Press; U.S.A.

Frank M. Galioto, Milton J. Reitman, Arnold J. Slovis & Irving A. Sarot; "Right coronary artery to left ventricle fistula: A case report and discussion"; American Heart Journal; Jul. 1971; pp. 93-97; vol. 82, No. 1; The C.V. Mosby Company; St. Louis, MO.

Joseph P. Archie Jr.; "Intramyocardial Pressure: Effect of Preload on Transmural Distribution of Systolic Coronary Blood Flow"; The American Journal of Cardiology; Jun. 1975; pp. 904-911; vol. 35; U.S.A.

L. Levinsky, T.Z. Lajos, A.B. Lee, Jr., C. Espersen, & G. Schimert; "The Revival of the Horseshoe Graft (Side-toSide Saphenous-Vein-to-Aorta Anastomosis"; The Thoracic and Cardiovascular Surgeon; Oct. 1979; pp. 322-324; vol. 27, No. 5; Georg Thieme Publishers; Stuttgart, Germany.

S. Sultan Ahmed, Bunyad Haider & Timothy J. Regan; "Silent left coronary artery-cameral fistula: probable cause of myocardial ischemia"; American Heart Journal; Oct. 1982; pp. 869-870; vol. 104, No. 4, pt. 1; The C.V. Mosby Company; St. Louis, MO.

Garrett Lee, Richard M. Ikeda, Jerold Theis, Daniel Stobbe, Claire Ogata, Henry Lui, Robert L. Reis, & Dean T. Mason; "Effects of laser Irradiation delivered by flexible fiberoptics system on the left ventricular internal myocardium"; American Heart Journal; Sep. 1983; pp. 587-590; vol. 106, No. 3; The C.V. Mosby Company; St. Louis, MO.

Julio C. Palmaz, Randy R. Sibbitt, Stewart R. Reuter, Francisco Garcia & Fremin O. Tio; "Expandable Intrahepatic Portacaval Shunt Stents: Early Experience in the Dog"; American Journal of Roentgenology; Oct. 1985; pp. 821-825; vol. 145; The American Roentgen Ray Society; U.S.A.

Goetz M. Richter, Gerd Noeldge, Julio C. Palmaz, Martin Roessle, Volker Slegerstetter, Martina Franke, Wolfgang Gerok, Werner Wenz & Edward Farthman; "Transjugular Intrahepatic Portacaval Stent Shunt: Preliminary Clinical Results"; Radiology; Mar. 1990; pp. 1027-1030; vol. 174, No. 3, Pt. 2; The Radiological Society of North America; Oak Brook, IL.

Gerald Zemel, Barry T. Katzen, Gary J. Becker, James F. Benenati & D. Skip Sallee; "Percutaneous Transjugular Portosystemic Shunt"; The Journal of the American Medical Association; Jul. 1991; 390-393; vol. 266, No. 3; American Medical Association; U.S.A.

Medical Industry Today Headline News; "Eclipse Gets OK to Pump Catheter Marketing in Europe"; Jul. 17, 1998; pp. 1-2; Article #07179802, Article is 349 words long; Medical Data International, Inc.; Santa Ana, CA.

Medical Industry Today Headline News; "Sales Dive, Losses Soar in 2Q for CardioGenesis"; Jul. 17, 1998; pp. 1-2; Article #07179808, Article is 560 words long; Medical Data International, Inc.; U.S.A.

Howard A. Cohen & Marco Zenati; "Alternative Approaches to Coronary Revascularization"; Current International Cardiology Reports; 1999; pp. 138-146; vol. 1; Current Science, Inc.; U.S.A.

Katherine S. Tweden, Frazier Eales, J. Douglas Cameron, Jerry C. Griffin, Eric E. Solien & Mark B. Knudson; "Ventriculocoronary Artery Bypass (VCAB), a Novel Approach to Myocardial Revascularization"; Feb. 2000; Article #2000-4653.

US 6,331,185, 12/2001, Gambale et al. (withdrawn)

* cited by examiner

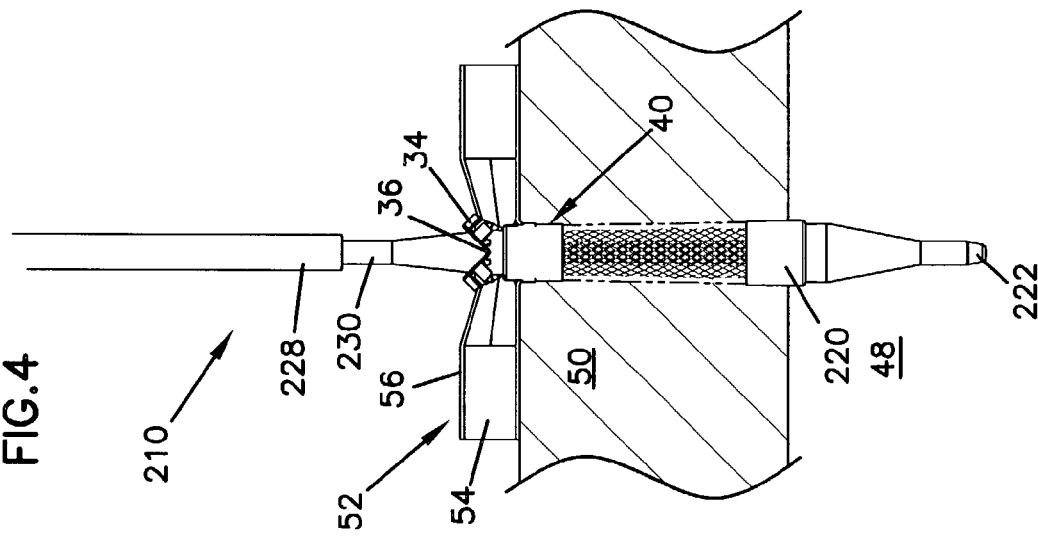
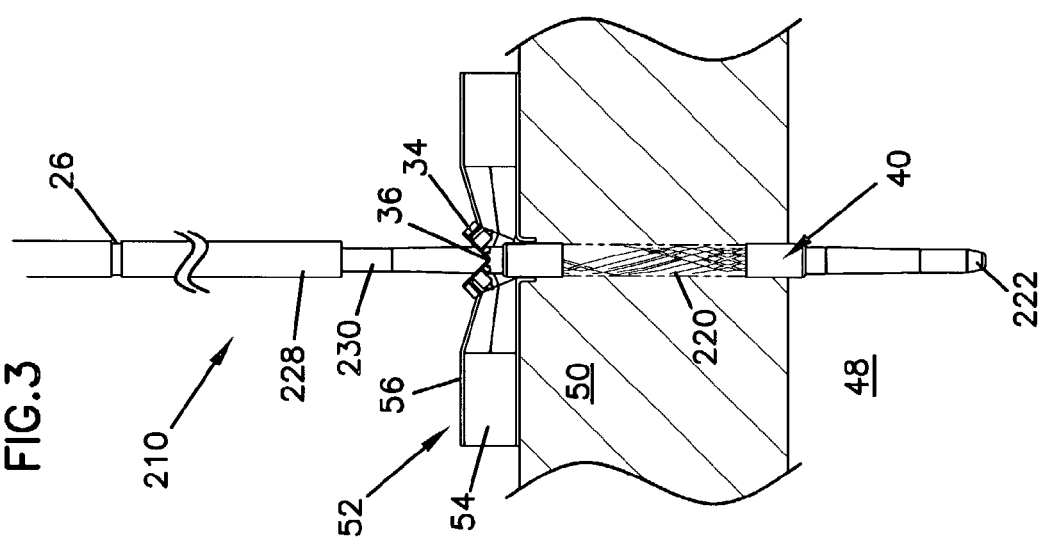
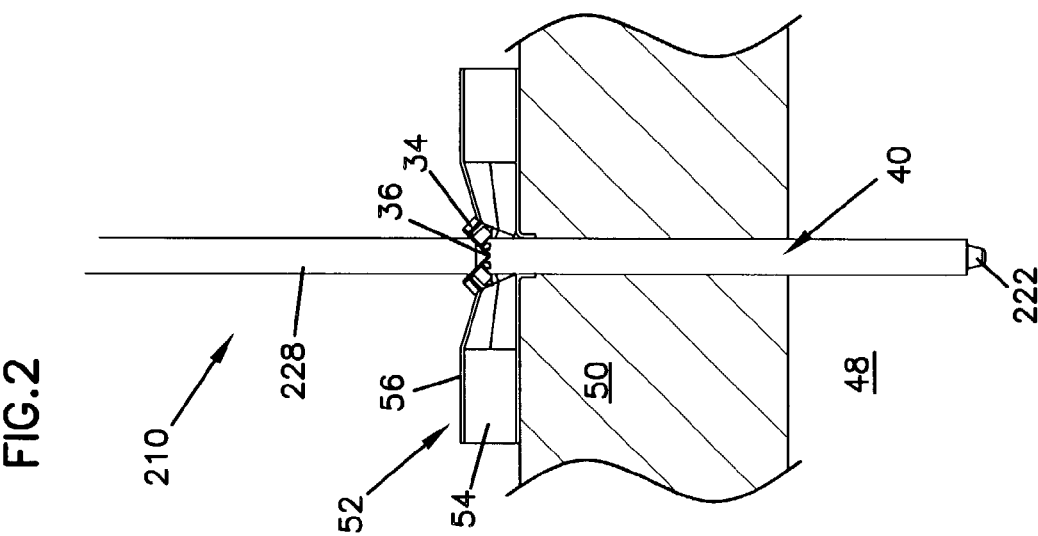

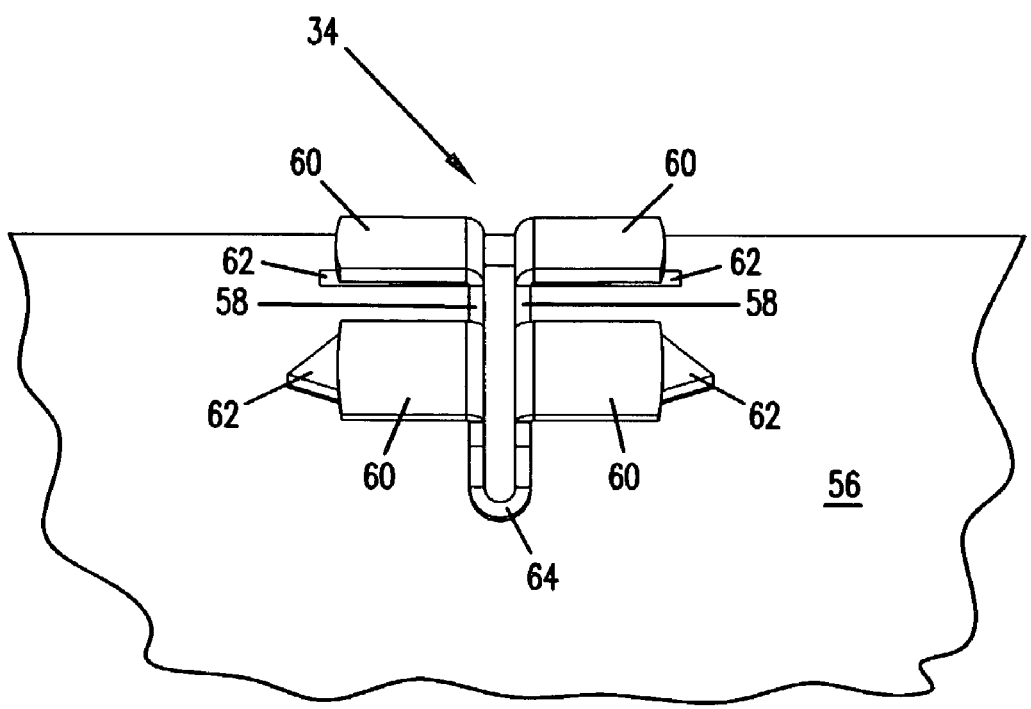
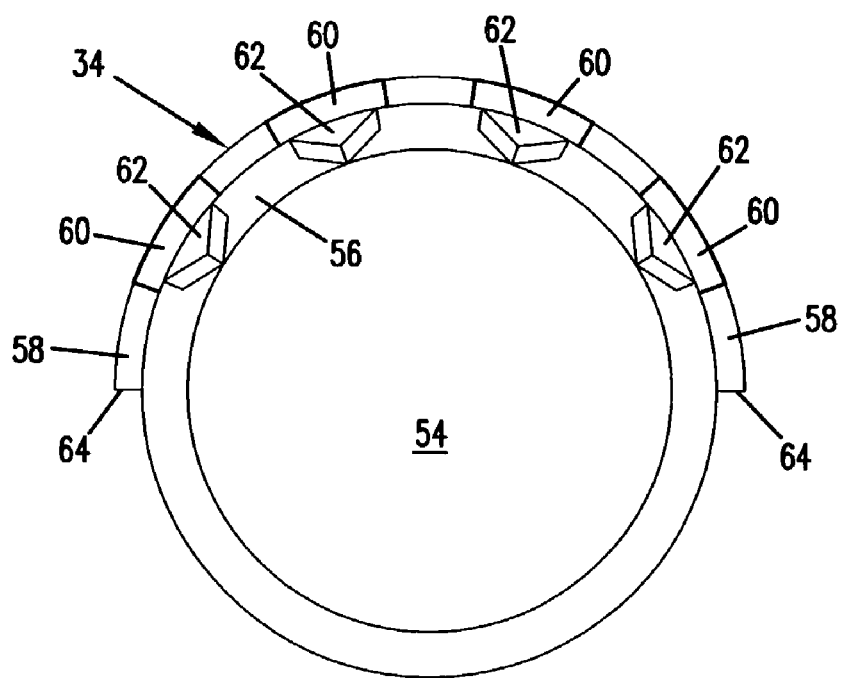

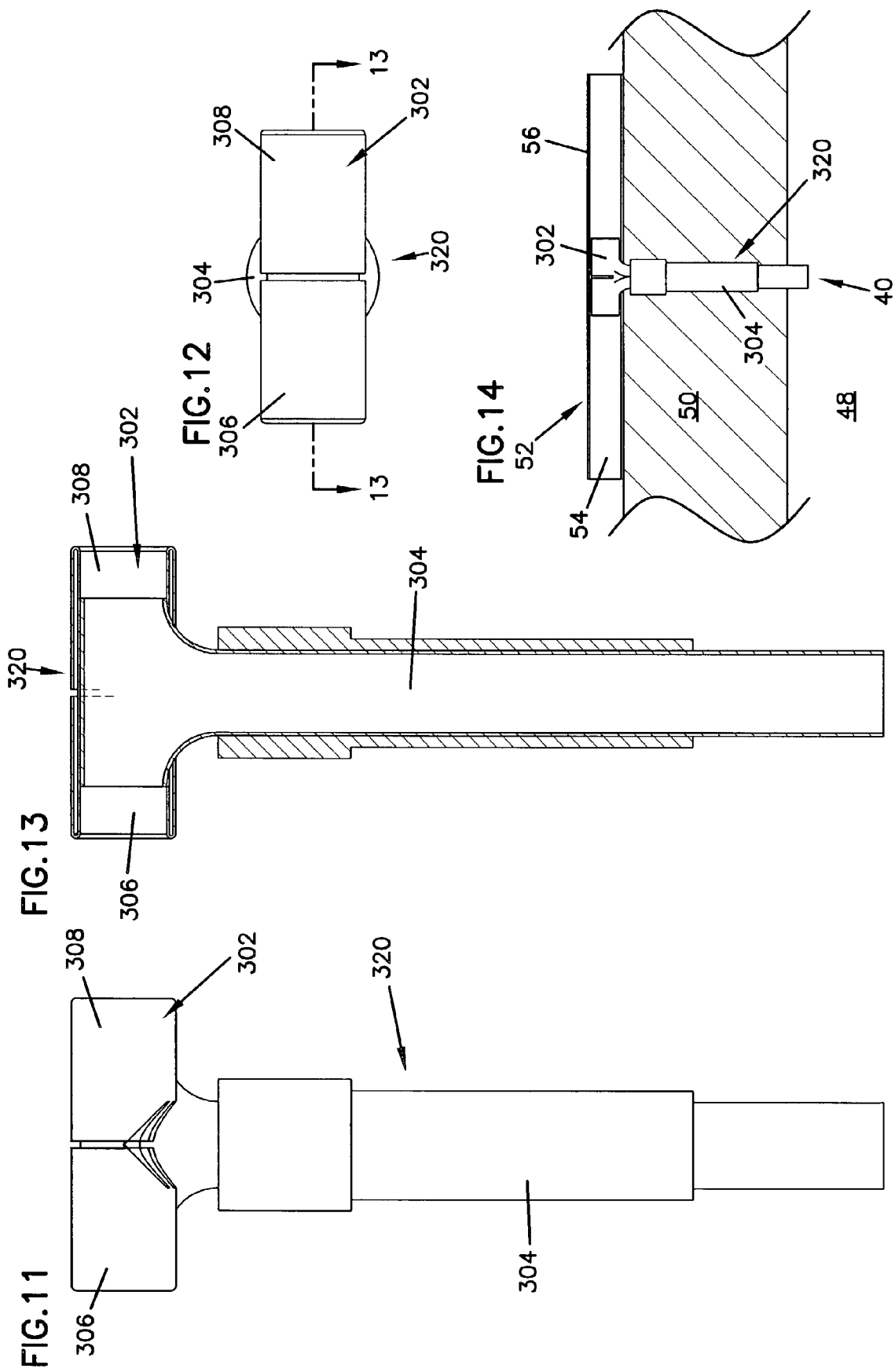

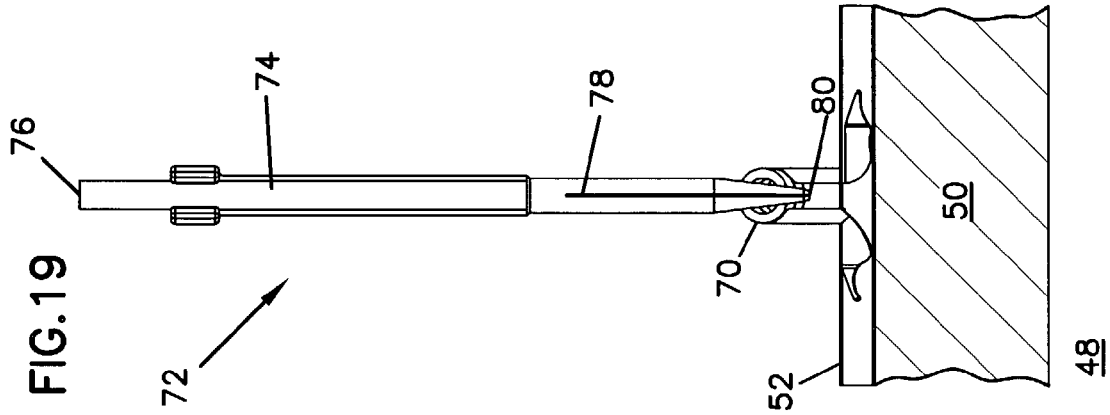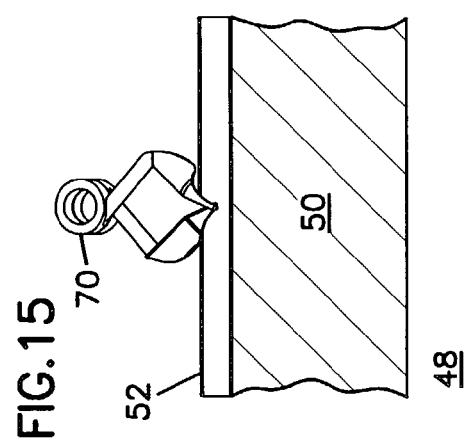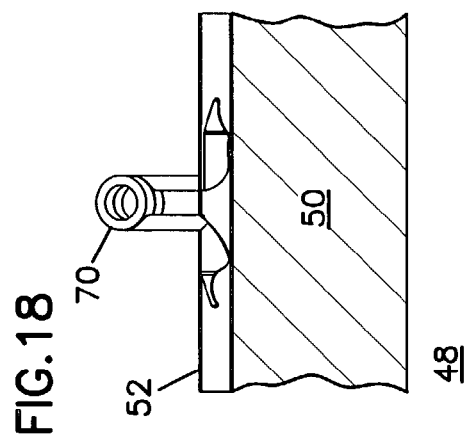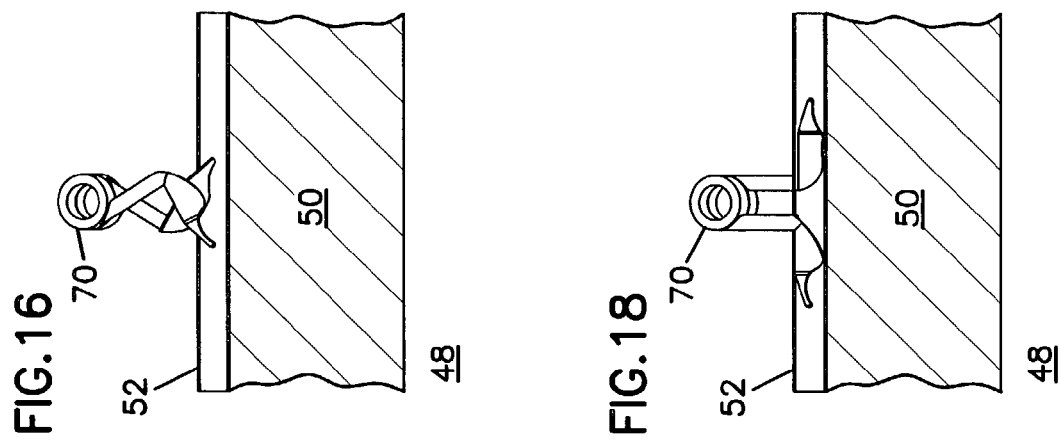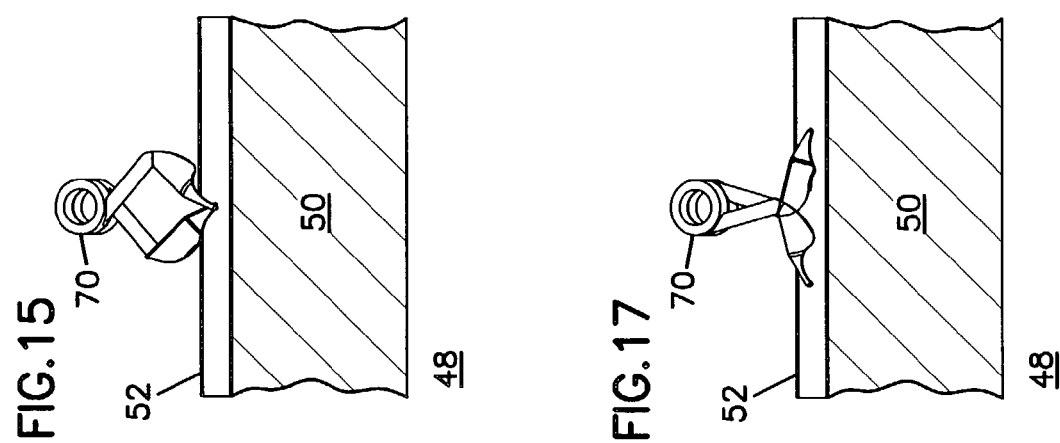

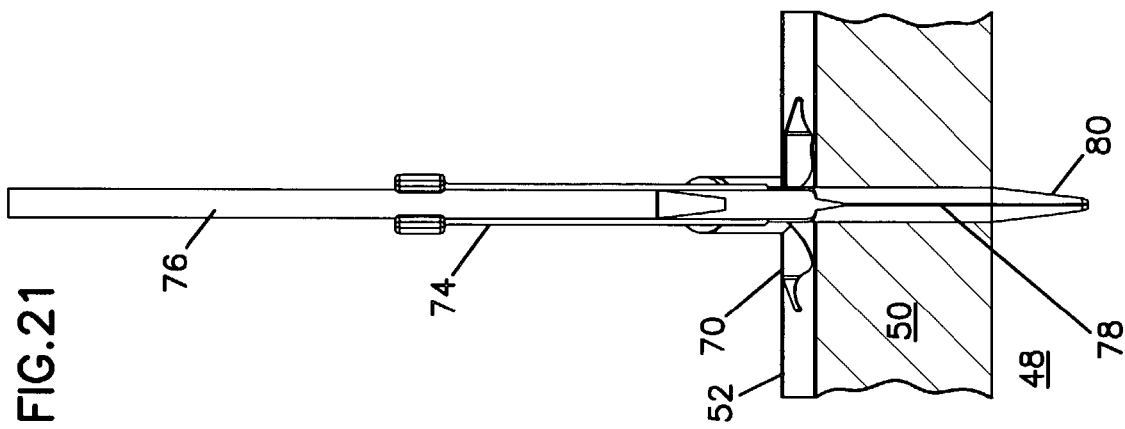
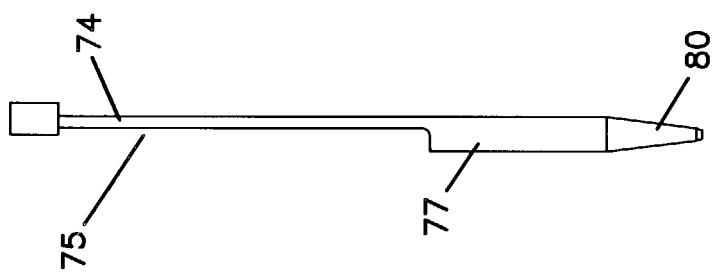
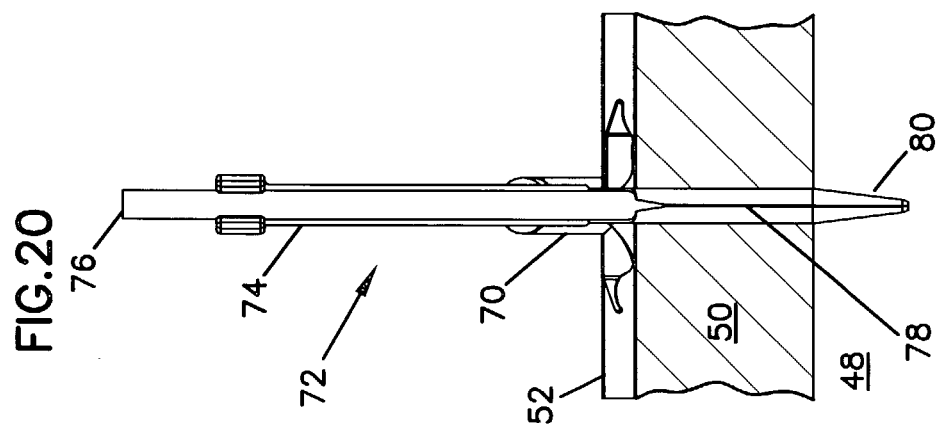

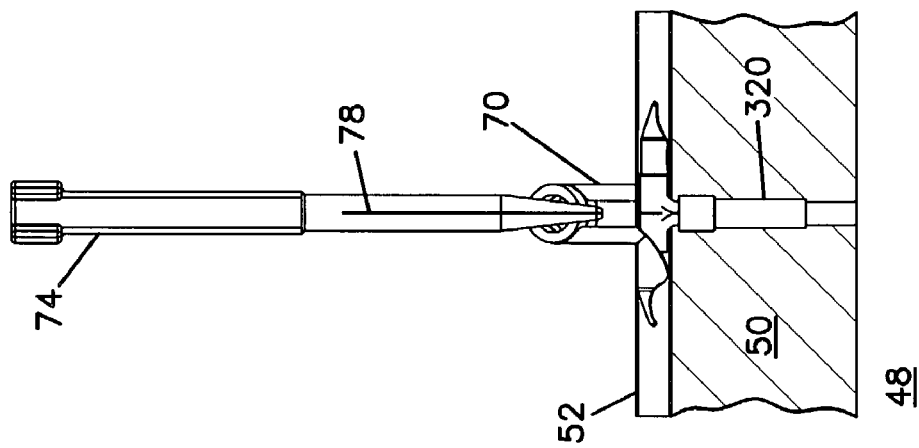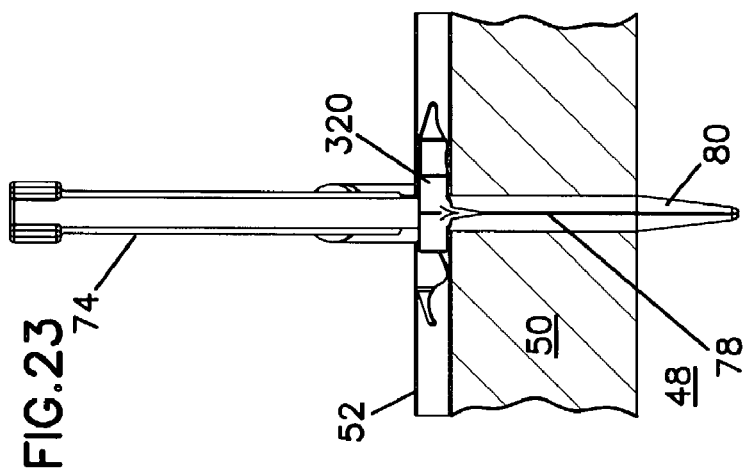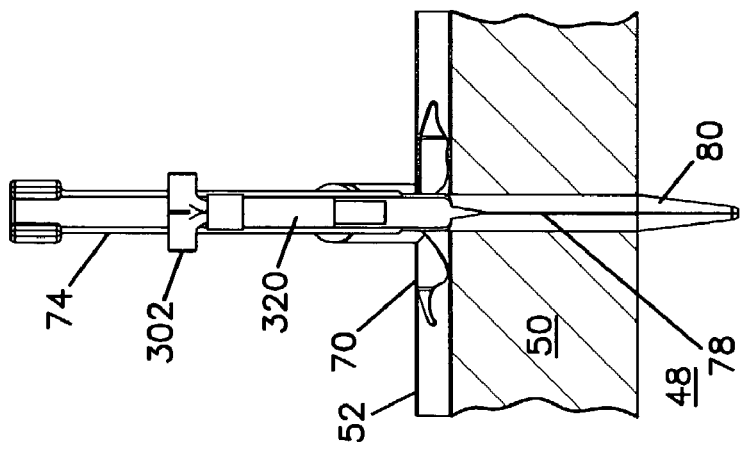

FIG. 30
FIG. 31
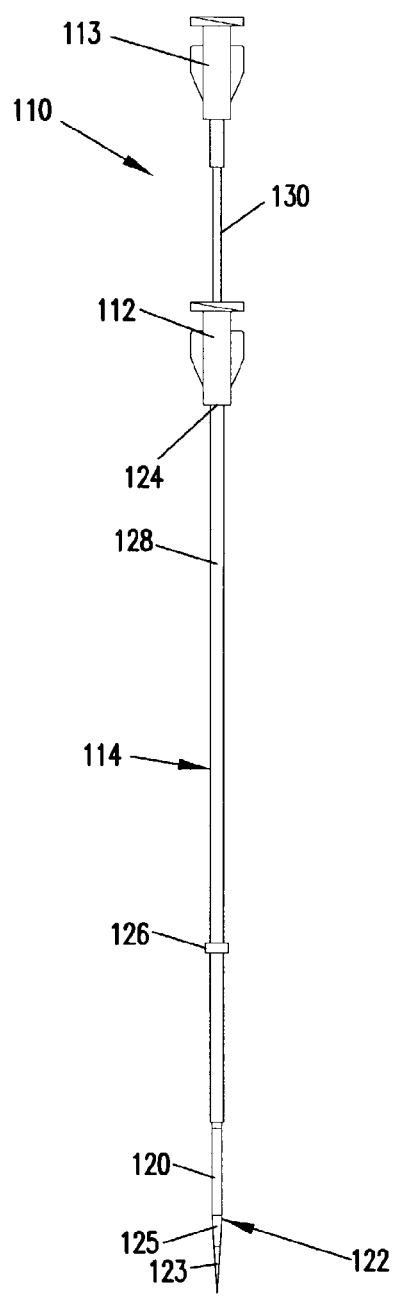
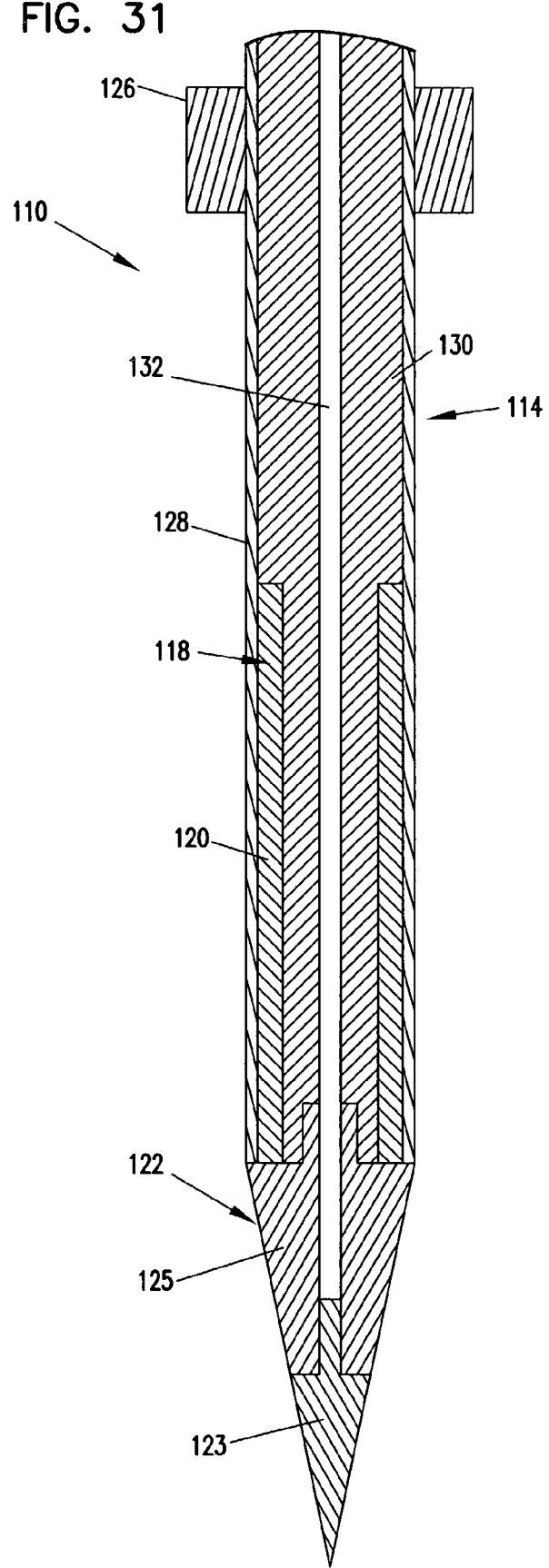

DEVICE FOR PLACING TRANSMYOCARDIAL IMPLANT

FIELD OF THE INVENTION

The present invention relates to placing devices in the myocardium of a patient. More specifically, the present invention relates to placement of devices through the myocardium for revascularizing occluded coronary vessels.

BACKGROUND OF THE INVENTION

Devices which are placed in the heart wall of a patient to revascularize an occluded coronary vessel as described in U.S. Pat. No. 5,944,019, the disclosure of which is incorporated herein by reference, are known. A variety of procedures for placing these devices have been described, including traditional by-pass open chest procedures, non-bypass open chest procedures, catheterization, and other non-open chest procedures. Improvements to the methods and apparatus used to place transmyocardial implants are desirable.

SUMMARY OF THE INVENTION

One aspect of the present disclosure relates to a transmyocardial implant placement device with an introducer, a transmyocardial implant mounted about the introducer, and a wound closure clip engaged to the introducer adjacent the transmyocardial implant. The introducer is adapted to be inserted through a coronary vessel and a myocardium of a patient into a chamber of the patient's heart and form a blood flow pathway through the myocardium between the heart chamber and the coronary vessel. When the introducer is inserted, the wound closure clip engages an outer wall of the coronary vessel and the transmyocardial implant extends from the heart chamber to the lumen of the coronary vessel. The transmyocardial implant is expanded in the blood flow pathway and the introducer retracted, leaving the transmyocardial implant in the within the blood flow pathway. As the introducer is retracted, the wound closure clip disengages from the introducer and closes an opening created by the introducer in the outer wall of the coronary vessel. Other inventive aspects are also disclosed herein.

BRIEF DESCRIPTION OF THE DRAWINGS

FIG. 2 is a schematic view of an alternative embodiment of a transmyocardial implant device according to the present invention inserted through a coronary vessel and a myocardium of a patient's heart into a heart chamber.

FIG. 3 is a schematic view of the transmyocardial implant device of FIG. 2, with an outer sheath retracted.

FIG. 4 is a schematic view of the transmyocardial implant device of FIG. 2, with the distal end of the device and the implant expanded.

FIG. 9 is an enlarged view of the wound closure clip of FIG. 8.

FIG. 10 is a partial cross-sectional view of the wound closure clip of FIG. 9.

FIG. 11 is a side view of an alternative embodiment of a transmyocardial implant according to the present invention.

FIG. 12 is a top view of the transmyocardial implant of FIG. 11.

FIG. 13 is a cross-sectional view of the transmyocardial implant taken along line 13-13 in FIG. 12.

FIG. 14 is a schematic view of the transmyocardial implant of FIG. 11 implanted in a myocardium.

FIGS. 15 through 29 illustrate a sequence of steps for insertion of the transmyocardial implant of FIG. 11 into an implantation site in a myocardium.

FIG. 30 is a side view of an alternative embodiment of a transmyocardial implant placement device according to the present invention.

FIG. 31 is a cross-sectional view of a distal end of the transmyocardial implant placement device of FIG. 30.

DETAILED DESCRIPTION

Transmyocardial implants or direct revascularization devices (DRD's) are known. DRD's have been placed in the heart wall to provide blood flow to areas of a patient's vascular system where flow has been impeded for some reason. Often, DRD's have been intended for use in improving or restoring blood flow to coronary vessels downstream of an arterial occlusion, as an alternative to more traditional vein graft bypass procedures. DRD's are also suitable for use in follow-up procedures for patients for whom an earlier vein graft by-pass failed, or for patients who are not suitable candidates for traditional vein graft by-pass procedures, such as diabetic patients or patients with significant circulatory problems.

I. First Embodiment

Figure 1:
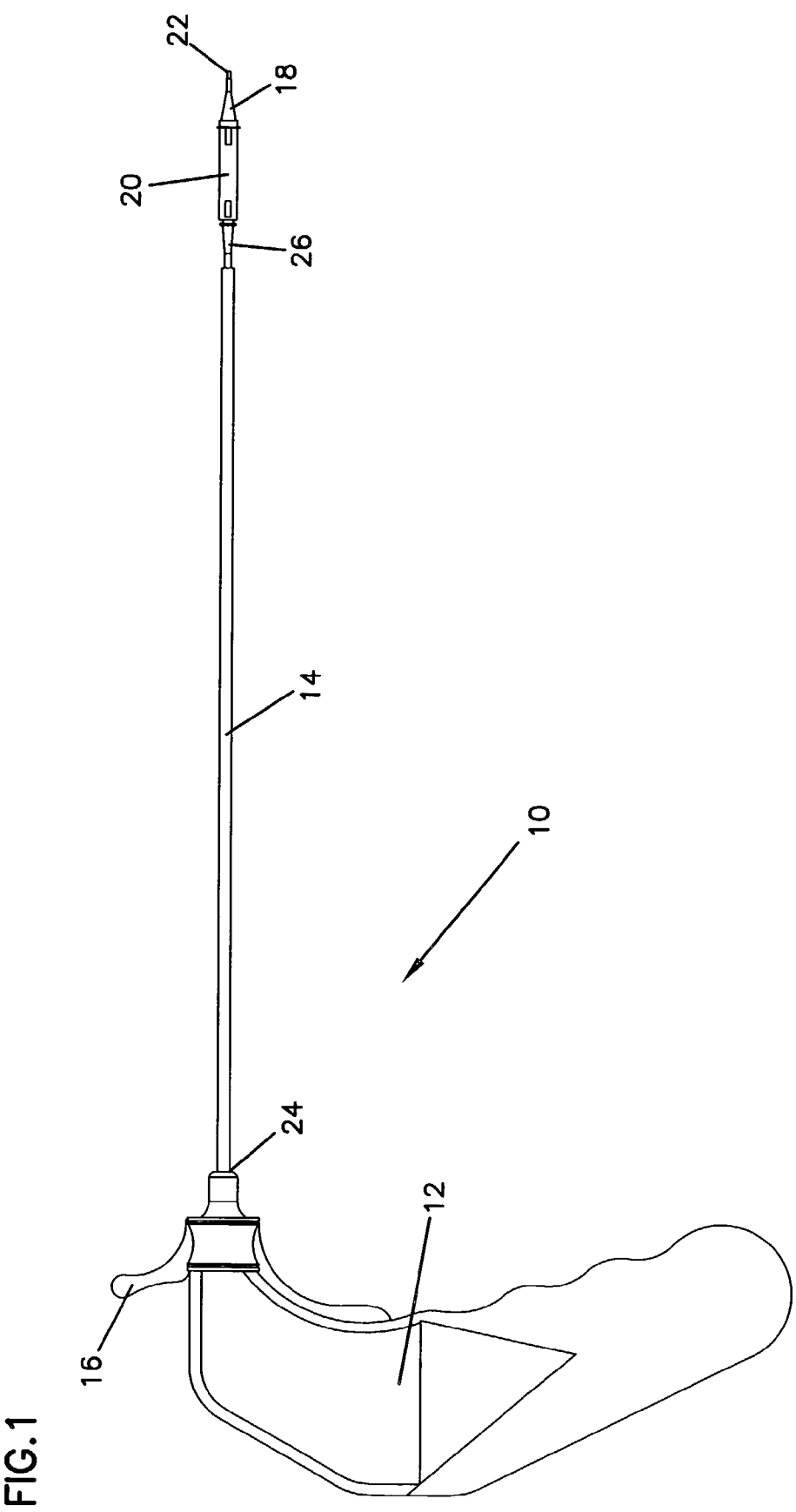
FIG. 1 is a side view of an embodiment of a transmyocardial implant placement device according to the present invention.

Regardless of the reason for use of DRD's, methods and apparatuses for placing the implants in a myocardium of a patient are required. One approach involves implanting DRD's through the myocardium in a traditional open chest procedure utilizing a by-pass machine. A device 10 of FIG. 1 has been developed to facilitate implanting implants within a myocardium. Device 10 could be used in an open chest procedure, but preferably is used in a thoracoscopic procedure which does not require pulmonary by-pass. Device 10 includes a handle 12, a shaft 14, an expander actuator 16 and an expander 18. Shaft 14 has a distal end 22 and a proximal end 24. Expander 18 is located proximate distal end 22 and is movable from a contracted position, as shown in FIG. 1 and a dilated position. Releasably mounted about expander 18 is an implant 20. Implant 20 is expandable between a collapsed shape, as shown in FIG. 1 and an expanded shape. Such expandable implants are known in the art and described in U.S. Pat. No. 5,755,682, issued May 26, 1998.

To place implant 20 at a site within a myocardium, distal end 22 is maneuvered adjacent the myocardium at the desired site. Distal end 22 is then advanced through the myocardium until implant 20 is positioned within the myocardium to provide fluid communication between a heart chamber on one side of the myocardium and a coronary vessel lying on an opposite side of the myocardium. Expander 18 is moved to the dilated position by actuator 16, expanding implant 20 from the collapsed shape to the expanded shape. Expander 18 is then moved back to the contracted position and distal end 22 of device 10 is removed from the myocardium.

Alternatively, implant 20 may be a self-expanding implant and expander 18 may be adapted to hold implant 20 in a collapsed shape until positioned within the myocardium. Actuator 16 would then release implant 20 from device 10, allowing implant 20 to expand within the myocardium and provide fluid communication between the heart chamber and the coronary vessel.

It is anticipated that device 10 may be adapted for use with or without a vessel closure device such as described herein below.

II. Second Embodiment

Figure 5:
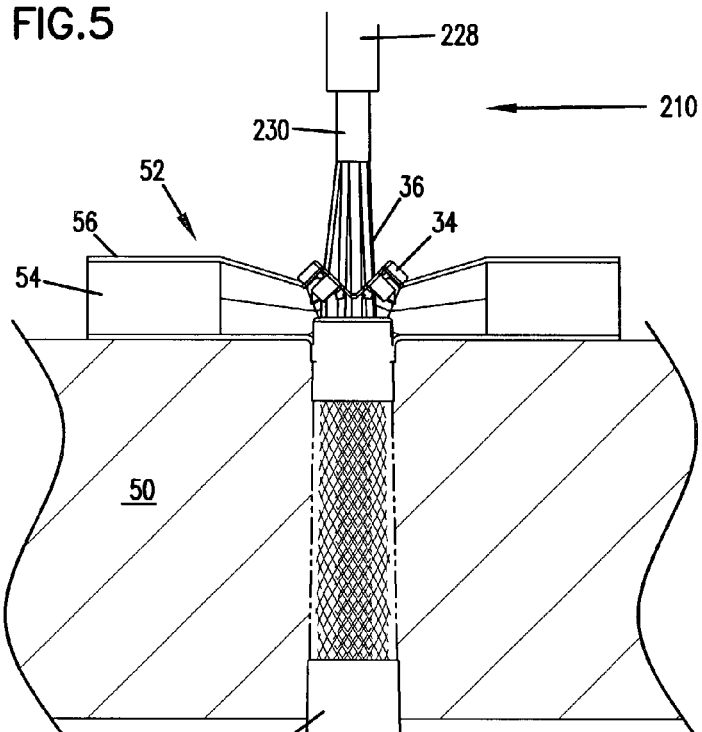
FIG. 5 is a schematic view of the transmyocardial implant device of FIG. 2, with the distal end of the device collapsed and the implant expanded.

FIGS. 2 through 8 show a first alternative device 210 and show a process for utilizing a transmyocardial implant placement device in accordance with the present invention. Device 210 may be used thoracoscopically to place an implant, as described below. Alternatively, device 210 may also be used in an open chest procedure, either on or off bypass-machine, preferably off bypass. Device 210 includes a shaft 214 with an outer sheath 228 and an inner catheter 230. Outer sheath 228 includes a clip slot 26 for releasably retaining wound closure clip 34. As shown in FIG. 5, inner catheter 230 includes a distal end 222 and an expander 218 proximate distal end 222. Implant 220 is releasably mounted about expander 218 and wound closure clip 34 is releasably mounted in clip slot 26.

To place an implant with device 210, distal end 222 forms and is inserted through an opening 36 in an outer wall 56 of a coronary vessel 52, through myocardium 50 of a patient into heart chamber 48, forming a blood flow pathway 40 from heart chamber 48 to lumen 54 of vessel 52. Device 210 is inserted far enough to allow wound closure clip 34 to engage outer wall 56 of vessel 52. Once clip 34 engages outer wall 56, outer sheath 228 is retracted, releasing clip 34 from clip slot 26 and exposing implant 220 within blood flow pathway 40. Expander 218 is then expanded, causing implant 220 to expand within blood flow pathway 40 and form a durable support for blood flow pathway 40. Expander 218 is then contracted to its insertion size, while implant 220 remains expanded, releasing implant 220 from inner catheter 230. Expander 218 may be any of a number of known devices which allow expansion and contraction by remote actuation, such as a balloon expander. Alternatively, it is anticipated that implant 220 can be made of a self-expanding material, such as nitinol. Such a self-expanding implant 220 would be releasably mounted to inner catheter 230 in a collapsed state until positioned within myocardium 50. Inner catheter 230 would not require expander 218, only a releasable mount to hold implant 220 in a collapsed state. When released from inner catheter 230, implant 220 would expand within blood flow pathway 40 as shown in FIG. 5.

Figure 6:
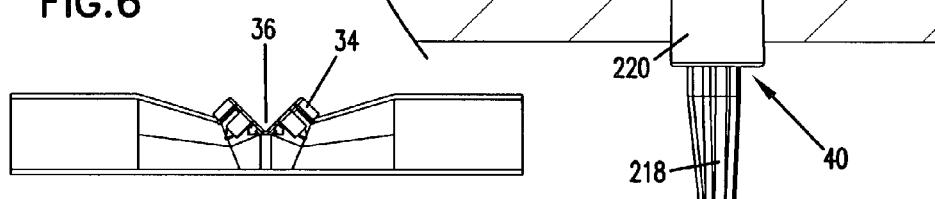
FIG. 6 is the schematic view of the transmyocardial implant device of FIG. 2, with the expanded implant in place in the myocardium, the device retracted and the wound closure clip open in the outer wall of the coronary vessel.
Figure 7:
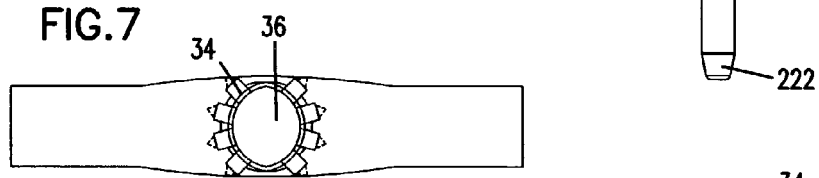
FIG. 7 is a top view of the wound closure clip of FIG. 6.
Figure 8:
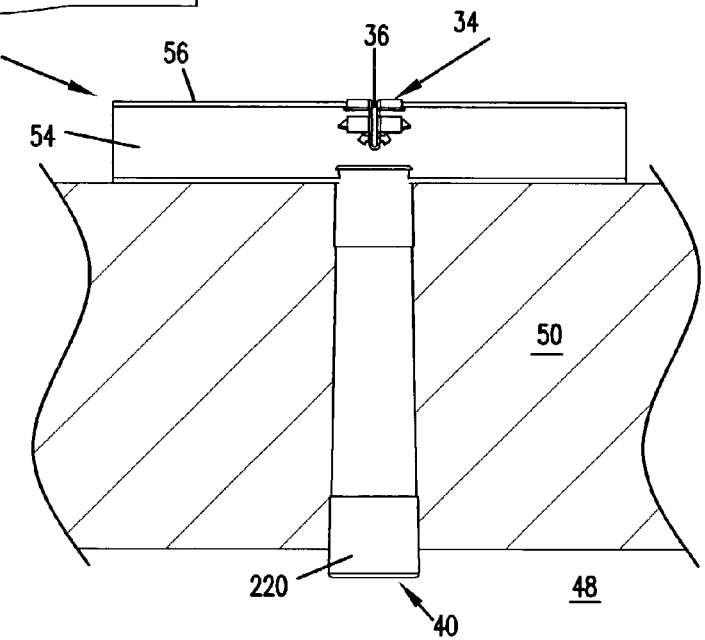
FIG. 8 is the schematic view of FIG. 6, with the wound closure clip closing the opening in the outer wall of the coronary vessel.
Figure 26:
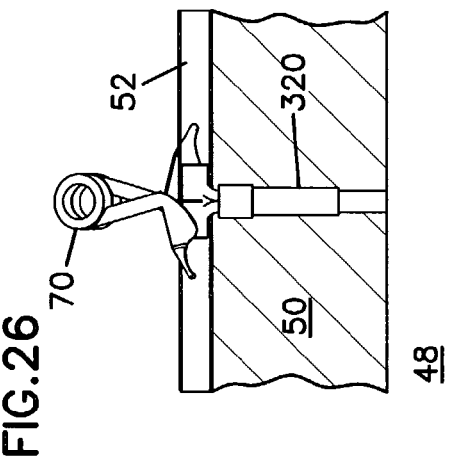
Figure 27:
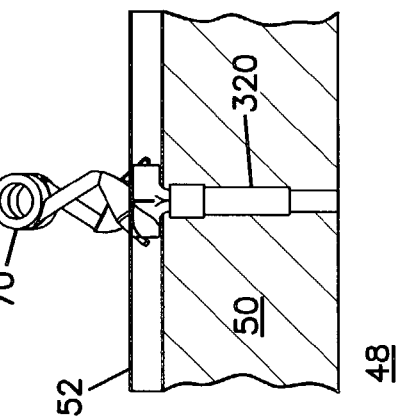
Figure 25:
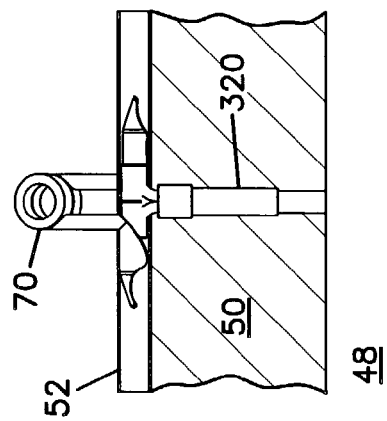

Device 210 can then be fully retracted from the patient's body leaving behind implant 220 within myocardium 50 and wound closure clip 34 in opening 36 in outer wall 56 of coronary vessel 52. Implant 220 is preferably sufficiently rigid to maintain blood flow pathway 40 open during both systole and diastole of the heart but may be collapsible in other embodiments. FIGS. 6 and 7 show a temporary open state of wound closure clip 34 and opening 36 after device 210 has been removed. Clip 34 is held in the open state by the presence of inner catheter 230 extending therethrough. Clip 34 is spring biased to close upon the removal of inner catheter 230. When clip 34 closes, opening 36 is pulled closed, thereby sealing blood flow out of vessel 52 at the site of insertion of device 210. Implant 220 remains in place within myocardium 50 and maintains blood flow path 40 between heart chamber 48 and lumen 54 of coronary vessel 52.

Wound closure clip 34 is similar to the autoanastomosis device disclosed and claimed in the jointly assigned U.S. patent application Ser. No. 09/768,930, filed Jan. 24, 2001, the disclosure of which is incorporate herein by reference. Wound closure clip 34 is formed of a flexible, resilient material that is biased toward to closed position shown in FIG. 8 but which may be temporarily deformed into an open position and mounted in clip slot 26, as shown in FIG. 2. Clip 34 is adapted to fixedly engage the sides of opening 36 in outer wall 56 of coronary vessel 52 upon insertion of device 210 into the position shown in FIG. 2. Once engaged to outer wall 56, clip 34 is held in an open position by inner catheter 230 passing through clip 34, as shown in FIGS. 2 through 5. Once device 210 has been retracted from clip 34, clip 34 returns to its biased closed position, carrying the edges of opening 26 in outer wall 56 to be adjacent each other and encourage rapid sealing and healing of opening 36. Clip 34 may be made of a bio-incorporated material or can be made of a more durable material such as nickel titanium alloy, provided that the material used has sufficient elastic characteristics to allow deformation about device 210 and return to a closed position upon retraction of device 210.

Additional detail of clip 34 is shown in FIGS. 7, 9 and 10. Clip 34 includes a pair of central ribs 58 which are joined at a hinge 64. When expanded to a fully open position, ribs 58 define a ring shape, as shown in FIG. 7. Extending from each rib 58 in opposite directions are one or more paddles 60. On a vessel side of each paddle 60 are tines 62 (i.e., teeth or barbs). FIGS. 9 and 10 show clip 34 engaging outer wall 56 of vessel 54 and closing opening 36. In FIG. 2, clip 34 is shown mounted about device 210 and opened. Tines 62 are angled with respect to paddles 60 so that when clip is mounted about device 210 as shown in FIG. 2, tines 62 engage outer wall 56 with a minimum of damage to outer wall 56 and allow clip 34 to pull opening 36 closed. As shown, tines 62 are angled away from rib 58. Alternatively, tines 62 could be angled to a greater or lesser extent away from rib 58 or angled toward rib 58. Ribs 58 are preferably made of a shape memory material or some type of resilient, deformable material which allows clip 34 to be opened for mounting about device 10, 110 or 210 and being biased closed when device 10, 110 or 210 is withdrawn.

III. Third Embodiment

An alternative embodiment of implant 320 is shown in FIGS. 11 through 14 including a tee-shaped extension 302 at an angle to a transmyocardial leg 304. When inserted as shown in FIG. 14, extension 302 lies axially within lumen 54 of vessel 52. Both extension 302 and leg 304 are hollow conduits allowing fluid communication within lumen 54 along the axial length of vessel 52 and between heart chamber 48 and lumen 54 of vessel 52, respectively. Leg 304 is preferably made of a material sufficiently rigid to resist collapse and able to maintain an open lumen during systole and diastole of the heart, but may be collapsible in other embodiments.

Implant 320 is inserted in a process shown in the FIGS. 15 through 29. A dilator 70 is placed through an incision in coronary vessel 52 as shown in FIGS. 15 through 18. Dilator 70 expands and opens the incision sufficiently to permit insertion of a device 72, which includes a shaft 76 and a guide 74, as shown in FIG. 19. Guide 74 includes a longitudinal split 78 beginning at a distal end 80. Guide 74 includes an open sided area 75 and a closed sided area 77, proximate distal end 80 through which split 78 extends, as shown in FIGS. 20 and 20A. Open sided area 75 permits insertion of implant 320 within closed sided area 77 for placement within myocardium 50, as described below.

Figure 29:
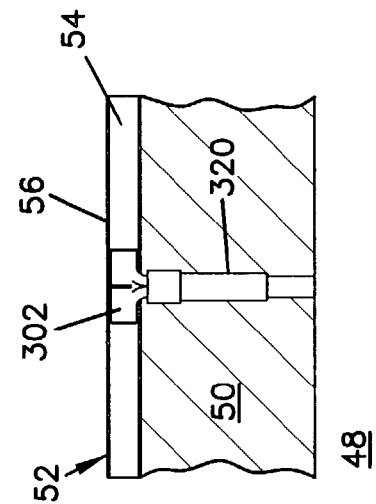
Figure 28:
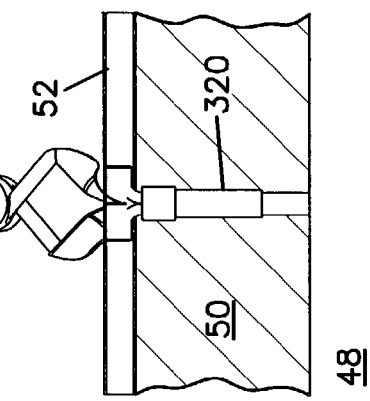

Shaft 76 is used to position guide 74 through dilator 70 within myocardium 50 so that distal end 80 extends into heart chamber 48, as shown in FIG. 20. Shaft 76 is then withdrawn, as shown in FIG. 21, and implant 320 is inserted through guide 74 to a position within myocardium 50, as shown in FIGS. 22 and 23. Guide 74 is then retracted from myocardium 50, as shown in FIG. 24, with split 78 opening to permit guide 74 to be removed without disturbing implant 320. Implant 320 is now permitting fluid communication between heart chamber 48 and lumen 54 of vessel 52. As shown in FIGS. 25 through 28, dilator 70 is collapsed and removed from the incision in vessel 52 and extension 302 helps seal the incision in vessel wall 56, reducing the need for mechanical closure devices, such as sutures, surgical adhesives, or clip 34, as shown in FIG. 29.

Implant 320 could also be adapted so that extension 302 extends different lengths on either side from transmyocardial leg 304, forming more of an L-shape as opposed to a T-shape.

IV. Fourth Embodiment

Referring now to FIGS. 30 and 31, another alternative placement device 110 is shown. Device 110 includes shaft 114 with an inner catheter 130 and an outer sheath 128. Handle 112 is attached to outer sheath 128 at proximal end 124 and handle 113 is attached to inner catheter 130. Inner catheter 130 includes an inner lumen 132 and is slidably retained within outer sheath 128. A self expanding implant 120 is mounted about inner catheter 130 in a implant receiving area 118 adjacent a distal end 122 and held in a collapsed form by outer sheath 128. Alternatively, implant 120 could be balloon-expandable and a balloon expander would be included at distal end 122 of inner catheter 130.

Distal end 122 includes a dilator 123 to ease insertion of the device 110 into a desired location of a patient's body and a transition element 125. Transition element 125 provides a transition of shaft 114 from the diameter of dilator 123 to the diameter of outer sheath 128 and Clip shoulder 126 is formed about outer sheath 128 at a position offset from distal end 122. A wound closure clip 34, as discussed previously, or similar device, may be releasably mounted about device 110 at clip shoulder 126. The extent of offset from distal end 122 is such that when device 110 is inserted within a heart to position stent 120 in the heart wall, wound closure clip 34 would engage outer wall 56 of blood vessel 52, as shown in FIG. 2. Inner lumen 132 may provides a pathway to inflate the balloon expander, if a balloon-expandable stent were used.

Device 110 is intended for use in a similar fashion to device 10, as shown in FIGS. 2 through 8, in placing implant 120 within myocardium 50 between vessel 56 and heart chamber 48. To place an implant 120 with device 110, distal end 122 is maneuvered proximate to the desired implantation site through outer wall 56 of vessel 52 and positioned so that implant 120 in a collapsed form underneath outer sheath 128 is correctly oriented at the implantation site in myocardium 50. Wound closure clip 34 at shoulder 126 would engage outer wall 56 of vessel 52. Retraction of outer sheath 128 proximally would release implant 120 and allow implant 120 to self expand to an expanded form. Retraction of outer sheath 128 would also leave wound closure clip 34 in place on outer wall 56. Once implant 120 is fully expanded, implant 120 is no longer held about device 110, allowing device 110 to be withdrawn from the patient's body. Withdrawal of device 110 would permit wound closure clip 34 to close and seal the opening in outer wall 56. Once expanded within at the implantation site, implant 120 is sufficiently rigid to resist collapse and maintain an open conduit during both systole and diastole of the heart.

Alternatively, implant 120 may be a balloon-expandable implant and a balloon expander included under implant receiving area 118. Device 110 could then be used in a fashion similar to that described above with regard to device 10 and shown in FIGS. 2 through 8.

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A transmyocardial implant placement device comprising:
   a catheter, with a distal end and a proximal end;
   a dilator mounted to the distal end of the catheter;
   an expander mounted to the catheter immediately proximal the dilator;
   a transmyocardial implant with a distal end and a proximal end, the transmyocardial implant having a collapsed condition and an expanded condition and mounted about the expander in the collapsed position; and
   a vessel wound closure clip positioned proximate to the proximal end of the collapsed transmyocardial implant.

2. The transmyocardial implant placement device of claim 1, wherein the catheter is adapted to be inserted through an outer wall of a coronary vessel, an inner wall of a coronary vessel and a myocardium of a patient into a chamber of the patient's heart and form a blood flow pathway through the myocardium between the heart chamber and lumen of the coronary vessel, with the wound closure clip engaging the outer wall of the coronary vessel and the transmyocardial implant extending from the heart chamber through the inner wall of the coronary vessel.

3. The transmyocardial implant placement device of claim 2, wherein the expander is adapted to expand the transmyocardial implant to the expanded condition so that the transmyocardial implant defines the blood flow pathway.

4. The transmyocardial implant placement device of claim 3, wherein the expander can be contracted and the catheter retracted from the myocardium, leaving the transmyocardial implant in the expanded condition within the blood flow pathway, releasing the wound closure clip as the catheter is retracted, the wound closure clip closing an opening created by the catheter in the outer wall of the coronary vessel.

5. The transmyocardial implant placement device of claim 1, wherein the transmyocardial implant in the expanded position within the myocardium maintains an open blood flow pathway during systole and diastole.

6. The transmyocardial implant placement device of claim 1, wherein the device includes an outer sheath about the catheter and the wound closure clip is releasably mounted to the outer sheath.

7. The transmyocardial implant placement device of claim 6, wherein the wound closure clip is releasably mounted to the outer sheath in a clip slot.

8. The transmyocardial implant placement device of claim 1, wherein the wound closure clip is movable between an open and a closed position wherein the clip is biased toward the closed position.

9. The transmyocardial implant placement device of claim 8, wherein the clip includes teeth adapted to embed in the outer wall of the coronary vessel and wherein the clip is adapted to pull the vessel opening closed when it moves from the open position to the closed position.

10. A transmyocardial implant placement device comprising:
   a rigid shaft;
   an expender mounted to the shaft, the expander expandable from a collapsed state to a dilated state and collapsible from the cilated state to the collapsed state;
   an actuator to actuate the expansion and collapse of the expander; and
   a myocardial implant adapted to be mounted within a myocardium and extend from a heart chamber to a lumen of a coronary vessel, the implant being expandable between a collapsed state and an expanded state, and the implant releasably mounted to the rigid shaft in the collapsed state so that the expander will expand the implant from the collapsed state to the expanded state,
   wherein a wound closure clip is releasably mounted to the rigid shaft proximal the implant and the actuator.

11. A method of implanting a transmyocardial implant comprising the steps of:
   providing an implant device with a shaft including the transmyocardial implant located proximate a distal end;
   inserting the distal end through an outer wall of a coronary vessel,
   an inner wall of the coronary vessel and a myocardium into a heart chamber, thereby creating an opening in the outer wall of the coronary vessel and also creating a passage between the heart chamber and a lumen of the vessel;
   implanting the implant within the passage; and
   withdrawing the distal end of the implant device from the myocardium and releasing a wound closure clip from about the shaft, the wound closure clip engaging the outer wall of the coronary vessel and drawing the opening closed as the implant device is withdrawn.

12. The method of claim 11, wherein the implant device includes the implant in a collapsed state and including the further step of actuating the transmyocardial implant from the collapsed state to an expanded state within the passage.

13. A method of implanting a transmyocardial implant within a myocardium comprising the steps of:
   incising an outer wall of a coronary vessel lying on an outer surface of the myocardium;
   forming a path through the myocardium between the coronary vessel and a heart chamber on an opposite surface of the myocardium with an implant placement guide inserted through the incision;
   inserting the transmyocardial implant within the guide until a hollow, open-ended myocardial leg of the implant is within the path and a hollow open-ended vessel portion of the implant is within a lumen of the coronary vessel, the myocardial leg and the vessel portion in fluid communication, the vessel portion including an upstream leg and a downstream leg, the legs extending axially within the lumen upstream and downstream from the myocardial leg;
   withdrawing the guide from the myocardium, the vessel portion remaining within the lumen allowing axial blood flow and aiding the closure of the incision, the myocardial leg being sufficiently rigid to remain open and in fluid communication with the vessel portion during systole and diastole.

14. The method of claim 13, wherein the myocardial leg extends beyond the myocardium into the heart chamber.

15. The method of claim 13, wherein the upstream leg and the downstream leg extend equal distances from the myocardial leg.

16. The method of claim 13, wherein the upstream leg and the downstream leg extend different distances from the myocardial leg.

* * * * *